(12) United States Patent
McIntyre

(10) Patent No.: US 9,169,317 B2
(45) Date of Patent: *Oct. 27, 2015

(54) METHOD OF ALTERING THE BINDING SPECIFICITY OF PLASMA PROTEINS BY OXIDATION-REDUCTION

(71) Applicant: REDOX-REACTIVE REAGENTS, LLC, Carmel, IN (US)

(72) Inventor: John A. McIntyre, Indianapolis, IN (US)

(73) Assignee: Redox-Reactive Reagents, LLC, Carmel, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/712,151

(22) Filed: Dec. 12, 2012

(65) Prior Publication Data

US 2013/0109838 A1    May 2, 2013

Related U.S. Application Data

(63) Continuation of application No. 12/107,819, filed on Apr. 23, 2008, now Pat. No. 8,334,146, which is a continuation-in-part of application No. 10/863,365, filed on Jun. 9, 2004, now Pat. No. 7,368,542, said application No. 12/107,819 is a continuation of application No. 11/359,489, filed on Feb. 23, 2006, now Pat. No. 7,892,751, which is a continuation-in-part of application No. 11/108,826, filed on Apr. 19, 2005, which is a continuation-in-part of application No. 10/863,365, filed on Jun. 9, 2004, now Pat. No. 7,368,542.

(60) Provisional application No. 60/476,607, filed on Jun. 9, 2003.

(51) Int. Cl.
| | | |
|---|---|---|
| C07K 17/00 | (2006.01) |
| C07K 16/00 | (2006.01) |
| C07K 16/18 | (2006.01) |
| G01N 33/53 | (2006.01) |
| G01N 33/537 | (2006.01) |
| G01N 33/564 | (2006.01) |
| G01N 33/68 | (2006.01) |

(52) U.S. Cl.
CPC .......... *C07K 16/00* (2013.01); *C07K 16/18* (2013.01); *G01N 33/5306* (2013.01); *G01N 33/5375* (2013.01); *G01N 33/564* (2013.01); *G01N 33/6854* (2013.01); *C07K 2317/21* (2013.01); *Y10S 424/81* (2013.01); *Y10S 436/825* (2013.01); *Y10S 530/868* (2013.01)

(58) Field of Classification Search
None
See application file for complete search history.

(56) References Cited

U.S. PATENT DOCUMENTS

| | | |
|---|---|---|
| 4,632,980 A | 12/1986 | Zee et al. |
| 4,703,001 A | 10/1987 | Vodian et al. |
| 4,950,612 A | 8/1990 | Khanna et al. |
| 5,061,790 A | 10/1991 | Elting |
| 5,939,394 A | 8/1999 | Fleming et al. |
| 5,980,954 A | 11/1999 | Bolton |
| 6,660,267 B1 | 12/2003 | Carroll |
| 6,932,969 B1 | 8/2005 | Bourel |
| 7,195,881 B2 | 3/2007 | Geffard |
| 7,368,542 B2 | 5/2008 | McIntyre |
| 2004/0082015 A1 | 4/2004 | Geffard |
| 2004/0101909 A1 | 5/2004 | Lemieux |
| 2005/0101016 A1 | 5/2005 | McIntyre |
| 2005/0260681 A1 | 11/2005 | McIntyre |

FOREIGN PATENT DOCUMENTS

| | | |
|---|---|---|
| CA | 2524325 | 3/2005 |
| EP | 0 778 025 | 6/1997 |
| JP | 502580/1990 | 8/1990 |
| JP | 517302/2000 | 12/2000 |
| WO | WO 89/05975 | 6/1989 |
| WO | WO 98/07436 | 2/1998 |
| WO | WO 00/74717 | 12/2000 |
| WO | WO 2004/111608 | 12/2004 |

OTHER PUBLICATIONS

Ischiropoulus, Harry et al, "Oxidative Stress and Nitration in Neurodegeneration: Cause, effect, or association?", J. Clin. Invest. 2003 111:pp. 163-169.

Smith, Mark A., et al, "Widespread Peroxynitrite-Mediated Damage in Alzheimer's Disease", *J. Neuroscience*, Apr. 15, 1997, 17(8) pp. 2653-2657.

McIntyre, John A., "The Appearance and Disappearance of Antiphospholipid Autoantibodies Subsequent to Oxidation-reduction Reactions", *Thrombosis Research* 2004, 114, pp. 579-587.

McIntyre, John A., et al, "Autoantibodies Unmasked by Redox Reactions", *J. Autoimmun* 2005; 24 pp. 311-317.

(Continued)

*Primary Examiner* — Yunsoo Kim
(74) *Attorney, Agent, or Firm* — Fitch, Even, Tabin and Flannery LLP

(57) ABSTRACT

The binding specificity of at least one plasma protein suspended or dissolved in a liquid medium is altered by exposing the protein to an oxidizing agent or an electric current sufficient to alter its binding specificity. A masked protein such as an autoantibody can be recovered from blood or blood products or extracts by oxidizing the protein to change its binding specificity.

5 Claims, 38 Drawing Sheets

(56) References Cited

OTHER PUBLICATIONS

McIntyre, John A., et al "Redox-reactive Autoantibodies: Detection and Physiological Relevance", Autoimmunity Reviews 2006; 5 pp. 76-83.
Sokol, D.K. et al, "Testing for Antiphospholipid Antibody (aPL) Specificities in Retrospective 'Normal' Cerebral Spinal Fluid (CSF)", *Clin Develop. Immunol.* 2005; 11: pp. 7-12.
Adams, J. Paige et al, "Molecular Psychology: Roles for the ERK MAP Kinase Cascade in Memory", *Annu. Rev. Pharmacol. Toxicol.* 2002 42 pp. 135-163.
Hindley, Alison et al, "Extracellular Signal Regulated Kinase (ERK)/mitogen Activated Protein Kinase (MAPK)-independent Functions of Raf Kinases", *J. Cell Science*, 2002; 115, pp. 1575-1581.
Cheung et al, "Emerging Role for ERK as a Key Regulator of Neuronal Apoptosis", *Science*, 2004; 251: pp. 1-3.
Chapman, J. et al, "Antiphospholipid Antibodies Permeablizie and Depolarize Brain Synaptoneurosomes", *Lupus* 1999; 8: pp. 127-133.
D'Aandrea, PhD, Michael R., "Evidence that Immunoglobulin-positive Neurons in Alzheimer's Disease are Dying Via the Classical Antibody-dependent Complement Pathway", *Am. J. Alzheimer's Dis. Other Dimentas* 2005; 20; pp. 144-150.
Colucci-D'Amato, L. et al, "Chronic Activation of ERK and Neurodegenerative Diseases", *Bioassays*, 2003: 25; pbs. 1085-1095.
www.ucsfhealth.org/childrens/edu/bottleWeaning.html , provided by UCSF Children's Hospital, Patient Education, Baby Bottle Weaning, 2002-2007.
Robertson and Greaves, Blood Rev 20: 2006, pp. 201-212.
Gallo et al., J. Neurol Sc. 122, 1994, pp. 97-101.
Tanne et al., Curr Rheumat Rep 3, 2001, pp. 286-292.
Jedryka-Goral. et al. Clin Rheumatol 19, 2000, pp. 306-310.
Mosek et al. Dem. Ger Cog. Disorder 11:, 2000, pp. 36-38.
Oomen et al. Psychiat Res 58, 1995, pp. 83-88.
Gomez-Puerta et al., Rheumatol 44:, 2005, pp. 95-99.
Sokol et al., Neurology 55: 2000, pp. 1379-1381.
Martinez-Cordero et al., J. Invest Allerg Clin Immunol 7, 1997, pp. 596-601.
McIntyre, John A., et al Redox-reactive Antiphospholipid Autoantibody Differences Between Serum From Alzheimer's Patient and Age-Matched Controls, Autoimmunity, Informa Healthcare, Dec. 18, 2009, pp. 1-7.
International Search Report Written Opinion PCT/US2007001582 dated Dec. 4, 2007.
Ischiropoulos et al. Oxidative Stress and Nitration in Neurodegeneration Cause, Effect, or Association?, J Clin Invest 111:pp. 163-169, 2003.
J. Cabiedes et al., Hidden Anti-Phospholipid Antibodies in Normal Human Sera Circulate as Immune Complexes Whose Antigen can be Removed by Heat, Acid, Hypermolar Buffers or Phospholipase Treatments, Eur. J. Immunol., 1998, Vo. 28, pp. 2108-2114.
Office Action of Japanese Patent Application No. 515229/2006 dated Dec. 16, 2008.
Office Action of Patent Office of the People's Republic of China Application No. 200480015987.9 dated Feb. 6, 2009.
EP Office Action dated App. No. 04 754 487.9 dated Mar. 5, 2009.
Canadian Office Action, Canadian Patent Application No. 2,602,635, Canadian Intellectual Property Office, Feb. 25, 2011.
Lacroix-Desmazes, et al., "Autoantibodies to factor VIII", Autoimmunity Reviews 1 (2002), pp. 105-110.
Ruffatti, et al., "Nuclear Membrane-Staining Antinuclear Antibody in Patients with Primary Biliary Cirrhosis", Journal of Clinical Immunology, vol. 5, No. 5, 1985.
Borg, et al., "protein tyrosine phosphatase-like protein IA2-antibodies plus glutamic acid decarboxylase 65 Antibodies (GADA) indicates autoimmunity as frequently as islet cell antibodies assay in children with recently diagnosed diabetes mellitus", Clinical Chemistry, vol. 43, No. 12, pp. 2358-2363.
Honnorat, et al., "Cellular Ataxia with Anti-Glutamic Acid Decarboxylase Antibodies", Archives or Neurology, vol. 48, No. 2, Feb. 2011, pp. 225-230.
Australian Examiner's Application No. 2004248155 dated Jun. 17, 2008.
International Preliminary Report of Appln. No. PCT/US07/01582 dated Aug. 22, 2008.
International Preliminary Report on Patentability, PCT/US2004/017889, Nov. 29, 2005.
International Search Report/Written Opinion, PCT/US2004/017889, Feb. 22, 2005.
International Search Report/Written Opinion, PCT/US2006/012802, Jan. 7, 2008.
Supplementary Partial European Search Report, EP 04 75 4487.9, Jun. 19, 2006.
Nagababu, et al., Formation of Fluorescent Heme Degradation Products during the Oxidation of Hemoglobin by Hydrogen Peroxide, Biochemical and Biophysical Research Communications 247, 1998, pp. 592-596.
Mosek, et al., Dementia and Antiphospholipid Antibodies, Dementia and Geriatric Cognitive Disorders, Jan./Feb. 2000, pp. 36-38.
Tanne, et al., Neurological Manifestations of the Antiphospholipid Syndrome, Current Rheumatology Reports, 2001, pp. 286-292.
Teunissen, et al., biochemical markers related to Alzheimer's dementia in serum and cerebrospinal fluid, Neurobiology of Aging, 23, 2002, pp. 485-508.
Hood, et al., Immunology, $2^{nd}$ Edition, Chapter 9: Immune Effector Mechanisms and the Complement System, The Benjamin/Cummings Publishing Company, Inc., 1984, pp. 334-336.
Pauling, Linus, General Chemistry: An Introduction to Descriptive Chemistry and Modern Chemical Theory, $2^{nd}$ Edition, W.H. Freeman and Company, p. 523, published 1953.
EPO Communication pursuant to Article 94(3) EPC, EP Application No. 07 749 017.5, Jan. 5, 2010.
Australian Examiner's first report on patent Application No. 2007225434, Aug. 24, 2009.
Canadian Office Action, Canadian Application No. 2,602,635, Sep. 9, 2009.
EPO Communication pursuant to Article 94(3) EPC, EP Application No. 04 754 487.9, Jul. 24, 2007.
EPO Communication pursuant to Article 94(3) EPC, EP Application No. 04 754 487.9, Apr. 9, 2008.
EPO Communication pursuant to Article 94(3) EPC, EP Application No. 04 754 487.9, Aug. 14, 2009.
EPO Communication pursuant to Article 94(3) EPC, EP Application No. 04 754 487.9, May 7, 2010.
Supplementary European Search Report, EP Application No. 07 749 017.5, Dec. 3, 2009.
Search Report of Indian App. No. 4760 filed on Oct. 25, 2007.
EPO Communication pursuant to Article 94(3) EPC, EP Application No. 04 754 487.9 dated Mar. 5, 2009.
Indian Office Action of Appln No. 4760/CHENP/2007 undated but faxed Sep. 10, 2008.
Conn et al., Outlines of Biochemistry, $4^{th}$ Edition, John Wiley & Sons, 1976, p. 23.
Canadian Office Action dated Feb. 24, 2015 in Canadian Patent Application No. 2,524,325.
Jean-Luc Seneca! and Yves Raymond, "Autoantibodies to Major and Minor Nuclear Lamins Are Not Restricted to Autoimmune Diseases", Clin Immunol Immunopathol., May 1992, 63(2):115-25.
M. Galli, et al., "Effect of Antiphospholipid Antibodies on Procoagulant Activity of Activated Platelets and Platelet-derived Microvesicles", Br J Haematol, Mar. 1993; 83(3):466-72.
Dawn Wagenknecht, et al., "The Evolution, Evaluation and Interpretation of Antiphospholipid Antibody Assays", Clinical Immunology Newsletter, 1995, vol. 15, No. 213 pp. 28-38.

In-house aPL ELISA*

| PS | CL | PE | PC |
|---|---|---|---|
| IgG | IgG | IgG | IgG |
| IgA | IgA | IgA | IgA |
| IgM | IgM | IgM | IgM |

\* In the presence (dependent) and absence (independent) of phospholipid-binding plasma proteins

Figure 1

Unconditioned broth + blood

Antiphospholipid Antibody (aPL) Results

| | | PL binding protein | | Normal ranges |
|---|---|---|---|---|
| | | dependent | independent | |
| aPS | IgG | 24 MoM +++ | 3 MoM | ≤ 4 MoM |
| | IgA | 8 MoM + | 2 MoM | ≤ 3 MoM |
| | IgM | 8 MoM + | 1 MoM | ≤ 5 MoM |
| aCL | IgG | 12 MoM +++ | 2 MoM | ≤ 4 MoM |
| | IgA | 12 MoM +++ | 2 MoM | ≤ 4 MoM |
| | IgM | 15 MoM +++ | 1 MoM | ≤ 6 MoM |
| aPE | IgG | 36 MoM +++ | 7 MoM + | ≤ 4 MoM |
| | IgA | 7 MoM + | 2 MoM | ≤ 3 MoM |
| | IgM | 8 MoM + | 3 MoM | ≤ 5 MoM |
| aPC | IgG | 2 MoM | 4 MoM | ≤ 4 MoM |
| | IgA | 1 MoM | 3 MoM | ≤ 3 MoM |
| | IgM | 6 MoM + | 5 MoM + | ≤ 4 MoM |

Figure 2 aPL range for 7 healthy persons

Antiphospholipid Antibody (aPL) Results

| | | PL binding protein | | Normal ranges |
|---|---|---|---|---|
| | | dependent | independent | |
| aPS | IgG | 17 - 25 +++ | 5 - 14 ++ | ≤ 4 MoM |
| | IgA | 4 - 14 ++ | 4 - 8 + | ≤ 3 MoM |
| | IgM | 5 - 16 ++ | 3 - 13 ++ | ≤ 5 MoM |
| aCL | IgG | 7 - 10 ++ | 1 - 3 | ≤ 4 MoM |
| | IgA | 6 - 19 ++ | 2 - 7 + | ≤ 4 MoM |
| | IgM | 6 - 17 ++ | 2 - 13 ++ | ≤ 6 MoM |
| aPE | IgG | 22 - 33 +++ | 7 - 20 ++ | ≤ 4 MoM |
| | IgA | 3 - 7 + | 1 - 5 + | ≤ 3 MoM |
| | IgM | 2 - 7 + | 2 - 8 + | ≤ 5 MoM |
| aPC | IgG | 1 - 2 | 1 - 4 | ≤ 4 MoM |
| | IgA | 1 - 4 + | 5 - 20 ++ | ≤ 3 MoM |
| | IgM | 1 - 8 + | 4 - 17 ++ | ≤ 4 MoM |

Figure 3

Horse RBC, human serum, broth

Antiphospholipid Antibody (aPL) Results

|  |  | PL binding protein | | Normal ranges |
|---|---|---|---|---|
|  |  | dependent | independent |  |
| aPS | IgG | 14 MoM +++ | 1 MoM | ≤ 4 MoM |
|  | IgA | 5 MoM + | 1 MoM | ≤ 3 MoM |
|  | IgM | 19 MoM +++ | 1 MoM | ≤ 5 MoM |
| aCL | IgG | 2 MoM | 1 MoM | ≤ 4 MoM |
|  | IgA | 13 MoM +++ | 1 MoM | ≤ 4 MoM |
|  | IgM | 27 MoM +++ | 1 MoM | ≤ 6 MoM |
| aPE | IgG | 1 MoM | 2 MoM | ≤ 4 MoM |
|  | IgA | 1 MoM | 1 MoM | ≤ 3 MoM |
|  | IgM | 1 MoM | 4 MoM | ≤ 5 MoM |
| aPC | IgG | 1 MoM | 1 MoM | ≤ 4 MoM |
|  | IgA | 1 MoM | 1 MoM | ≤ 3 MoM |
|  | IgM | 1 MoM | 1 MoM | ≤ 4 MoM |

Figure 4

Human RBC, horse serum, broth

Antiphospholipid Antibody (aPL) Results

| | | PL binding protein | | Normal ranges |
|---|---|---|---|---|
| | | dependent | independent | |
| aPS | IgG | 1 MoM | 1 MoM | ≤ 4 MoM |
| | IgA | 1 MoM | 1 MoM | ≤ 3 MoM |
| | IgM | 1 MoM | 1 MoM | ≤ 5 MoM |
| aCL | IgG | 1 MoM | 1 MoM | ≤ 4 MoM |
| | IgA | 1 MoM | 1 MoM | ≤ 4 MoM |
| | IgM | 1 MoM | 1 MoM | ≤ 6 MoM |
| aPE | IgG | 1 MoM | 1 MoM | ≤ 4 MoM |
| | IgA | 1 MoM | 1 MoM | ≤ 3 MoM |
| | IgM | 1 MoM | 1 MoM | ≤ 5 MoM |
| aPC | IgG | 1 MoM | 1 MoM | ≤ 4 MoM |
| | IgA | 1 MoM | 1 MoM | ≤ 3 MoM |
| | IgM | 1 MoM | 1 MoM | ≤ 4 MoM |

Figure 5

Blood in rocking vial at 22° C

Antiphospholipid Antibody (aPL) Results

|  |  | PL binding protein | | Normal ranges |
|---|---|---|---|---|
|  |  | dependent | independent |  |
| aPS | IgG | 6 MoM + | 3 MoM | ≤ 4 MoM |
|  | IgA | 1 MoM | 1 MoM | ≤ 3 MoM |
|  | IgM | 1 MoM | 1 MoM | ≤ 5 MoM |
| aCL | IgG | 2 MoM | 2 MoM | ≤ 4 MoM |
|  | IgA | 1 MoM | 1 MoM | ≤ 4 MoM |
|  | IgM | 1 MoM | 1 MoM | ≤ 6 MoM |
| aPE | IgG | 4 MoM | 1 MoM | ≤ 4 MoM |
|  | IgA | 1 MoM | 1 MoM | ≤ 3 MoM |
|  | IgM | 1 MoM | 1 MoM | ≤ 5 MoM |
| aPC | IgG | 2 MoM | 2 MoM | ≤ 4 MoM |
|  | IgA | 1 MoM | 1 MoM | ≤ 3 MoM |
|  | IgM | 1 MoM | 6 MoM + | ≤ 4 MoM |

Figure 6

Replace charcoal: 0.7mm Degalan

Antiphospholipid Antibody (aPL) Results

|  |  | PL binding protein | | Normal ranges |
|---|---|---|---|---|
|  |  | dependent | independent | |
| aPS | IgG | 31 MoM +++ | 3 MoM | ≤ 4 MoM |
|  | IgA | 3 MoM | 1 MoM | ≤ 3 MoM |
|  | IgM | 2 MoM | 1 MoM | ≤ 5 MoM |
| aCL | IgG | 7 MoM + | 2 MoM | ≤ 4 MoM |
|  | IgA | 5 MoM + | 2 MoM | ≤ 4 MoM |
|  | IgM | 10 MoM +++ | 1 MoM | ≤ 6 MoM |
| aPE | IgG | 8 MoM + | 1 MoM | ≤ 4 MoM |
|  | IgA | 2 MoM | 1 MoM | ≤ 3 MoM |
|  | IgM | 1 MoM | 1 MoM | ≤ 5 MoM |
| aPC | IgG | 2 MoM | 1 MoM | ≤ 4 MoM |
|  | IgA | 1 MoM | 1 MoM | ≤ 3 MoM |
|  | IgM | 1 MoM | 4 MoM | ≤ 4 MoM |

Figure 7

Blood in stationary vial at 37° C

Antiphospholipid Antibody (aPL) Results

| | | PL binding protein | | Normal ranges |
|---|---|---|---|---|
| | | dependent | independent | |
| aPS | IgG | 1 MoM | 1 MoM | ≤ 4 MoM |
| | IgA | 1 MoM | 1 MoM | ≤ 3 MoM |
| | IgM | 2 MoM | 1 MoM | ≤ 5 MoM |
| aCL | IgG | 1 MoM | 1 MoM | ≤ 4 MoM |
| | IgA | 1 MoM | 1 MoM | ≤ 4 MoM |
| | IgM | 7 MoM + | 1 MoM | ≤ 6 MoM |
| aPE | IgG | 1 MoM | 1 MoM | ≤ 4 MoM |
| | IgA | 1 MoM | 1 MoM | ≤ 3 MoM |
| | IgM | 4 MoM | 3 MoM | ≤ 5 MoM |
| aPC | IgG | 1 MoM | 3 MoM | ≤ 4 MoM |
| | IgA | 1 MoM | 1 MoM | ≤ 3 MoM |
| | IgM | 3 MoM | 7 MoM + | ≤ 4 MoM |

Figure 8

Effect of heating at 56° C

Antiphospholipid Antibody (aPL) Results

| | | PL binding protein | | PL binding protein | Normal ranges |
|---|---|---|---|---|---|
| | | preheat | | heated | |
| aPS | IgG | 47 MoM +++ | | 69 MoM +++ | ≤ 4 MoM |
| | IgA | 12 MoM +++ | | 18 MoM +++ | ≤ 3 MoM |
| | IgM | 3 MoM | | 1 MoM | ≤ 5 MoM |
| aCL | IgG | 13 MoM +++ | | 16 MoM +++ | ≤ 4 MoM |
| | IgA | 16 MoM +++ | | 22 MoM +++ | ≤ 4 MoM |
| | IgM | 12 MoM +++ | | 16 MoM +++ | ≤ 6 MoM |
| aPE | IgG | 48 MoM +++ | | 44 MoM +++ | ≤ 4 MoM |
| | IgA | 8 MoM + | | 8 MoM + | ≤ 3 MoM |
| | IgM | 2 MoM | | 1 MoM | ≤ 5 MoM |
| aPC | IgG | 5 MoM + | | 6 MoM + | ≤ 4 MoM |
| | IgA | 1 MoM | | 2 MoM | ≤ 3 MoM |
| | IgM | 1 MoM | | 3 MoM | ≤ 4 MoM |

Figure 9

Becton Dickinson* culture vial (*Replacing Biomerieux)

Antiphospholipid Antibody (aPL) Results

| | | PL binding protein | | Normal ranges |
|---|---|---|---|---|
| | | dependent | independent | |
| aPS | IgG | 11 MoM +++ | 3 MoM | ≤ 4 MoM |
| | IgA | failure | failure | ≤ 3 MoM |
| | IgM | 4 MoM | 1 MoM | ≤ 5 MoM |
| aCL | IgG | 6 MoM + | 4 MoM | ≤ 4 MoM |
| | IgA | 5 MoM + | 5 MoM + | ≤ 4 MoM |
| | IgM | 9 MoM + | 1 MoM | ≤ 6 MoM |
| aPE | IgG | 32 MoM +++ | 1 MoM | ≤ 4 MoM |
| | IgA | 2 MoM | 1 MoM | ≤ 3 MoM |
| | IgM | 10 MoM +++ | 1 MoM | ≤ 5 MoM |
| aPC | IgG | 1 MoM | 1 MoM | ≤ 4 MoM |
| | IgA | 1 MoM | 1 MoM | ≤ 3 MoM |
| | IgM | 1 MoM | 1 MoM | ≤ 4 MoM |

Figure 10

Anaerobic culture vial broth + blood

Antiphospholipid Antibody (aPL) Results

|  |  | PL binding protein | | Normal ranges |
|---|---|---|---|---|
|  |  | dependent | independent |  |
| aPS | IgG | 16 MoM +++ | 10 MoM +++ | ≤ 4 MoM |
|  | IgA | 3 MoM | 2 MoM | ≤ 3 MoM |
|  | IgM | 9 MoM + | 5 MoM | ≤ 5 MoM |
| aCL | IgG | 8 MoM + | 3 MoM | ≤ 4 MoM |
|  | IgA | 4 MoM | 1 MoM | ≤ 4 MoM |
|  | IgM | 17 MoM +++ | 3 MoM | ≤ 6 MoM |
| aPE | IgG | 33 MoM +++ | 10 MoM +++ | ≤ 4 MoM |
|  | IgA | 4 MoM + | 1 MoM | ≤ 3 MoM |
|  | IgM | 9 MoM + | 3 MoM | ≤ 5 MoM |
| aPC | IgG | 1 MoM | 2 MoM | ≤ 4 MoM |
|  | IgA | 1 MoM | 1 MoM | ≤ 3 MoM |
|  | IgM | 3 MoM | 5 MoM + | ≤ 4 MoM |

Figure 11

Replace RBC with K562

(K562 cell count 11.3x10$^6$)

Antiphospholipid Antibody (aPL) Results

|  |  | PL binding protein | | Normal ranges |
|---|---|---|---|---|
|  |  | dependent | independent |  |
| aPS | IgG | 10 MoM +++ | 6 MoM + | ≤ 4 MoM |
|  | IgA | 5 MoM + | 1 MoM | ≤ 3 MoM |
|  | IgM | 1 MoM | 1 MoM | ≤ 5 MoM |
| aCL | IgG | 3 MoM | 1 MoM | ≤ 4 MoM |
|  | IgA | 7 MoM + | 1 MoM | ≤ 4 MoM |
|  | IgM | 2 MoM | 1 MoM | ≤ 6 MoM |
| aPE | IgG | 14 MoM +++ | 4 MoM | ≤ 4 MoM |
|  | IgA | 7 MoM + | 2 MoM | ≤ 3 MoM |
|  | IgM | 1 MoM | 1 MoM | ≤ 5 MoM |
| aPC | IgG | 1 MoM | 2 MoM | ≤ 4 MoM |
|  | IgA | 1 MoM | 3 MoM | ≤ 3 MoM |
|  | IgM | 1 MoM | 3 MoM | ≤ 4 MoM |

Figure 12

Replace broth with RPMI and beads

Antiphospholipid Antibody (aPL) Results

|  |  | PL binding protein | | Normal ranges |
|---|---|---|---|---|
|  |  | dependent | independent |  |
| aPS | IgG | 1 MoM | 1 MoM | ≤ 4 MoM |
|  | IgA | 1 MoM | 1 MoM | ≤ 3 MoM |
|  | IgM | 2 MoM | 2 MoM | ≤ 5 MoM |
| aCL | IgG | 1 MoM | 2 MoM | ≤ 4 MoM |
|  | IgA | 1 MoM | 1 MoM | ≤ 4 MoM |
|  | IgM | 2 MoM | 2 MoM | ≤ 6 MoM |
| aPE | IgG | 1 MoM | 1 MoM | ≤ 4 MoM |
|  | IgA | 1 MoM | 1 MoM | ≤ 3 MoM |
|  | IgM | 2 MoM | 4 MoM | ≤ 5 MoM |
| aPC | IgG | 1 MoM | 1 MoM | ≤ 4 MoM |
|  | IgA | 1 MoM | 1 MoM | ≤ 3 MoM |
|  | IgM | 3 MoM | 5 MoM + | ≤ 4 MoM |

Figure 13

Placental cord blood + broth

Antiphospholipid Antibody (aPL) Results

|  |  | PL binding protein | | Normal ranges |
|---|---|---|---|---|
|  |  | dependent | independent |  |
| aPS | IgG | 42 MoM +++ | 27 MoM +++ | < 4 MoM |
|  | IgA | 1 MoM | 1 MoM | < 3 MoM |
|  | IgM | 1 MoM | 1 MoM | < 5 MoM |
| aCL | IgG | 14 MoM +++ | 6 MoM + | < 4 MoM |
|  | IgA | 1 MoM | 1 MoM | < 4 MoM |
|  | IgM | 2 MoM | 1 MoM | < 6 MoM |
| aPE | IgG | 38 MoM +++ | 23 MoM +++ | < 4 MoM |
|  | IgA | 1 MoM | 1 MoM | < 3 MoM |
|  | IgM | 1 MoM | 1 MoM | < 5 MoM |
| aPC | IgG | 1 MoM | 6 MoM + | < 4 MoM |
|  | IgA | 1 MoM | 1 MoM | < 3 MoM |
|  | IgM | 1 MoM | 1 MoM | < 4 MoM |

Figure 14

Replace RBC with sodium 200μM nitroprusside

Antiphospholipid Antibody (aPL) Results

| | | PL binding protein | | Normal ranges |
|---|---|---|---|---|
| | | dependent | independent | |
| aPS | IgG | 18 MoM +++ | 5 MoM + | ≤ 4 MoM |
| | IgA | 8 MoM + | 4 MoM + | ≤ 3 MoM |
| | IgM | 1 MoM | 1 MoM | ≤ 5 MoM |
| aCL | IgG | 7 MoM + | 1 MoM | ≤ 4 MoM |
| | IgA | 7 MoM | 1 MoM | ≤ 4 MoM |
| | IgM | 1 MoM | 1 MoM | ≤ 6 MoM |
| aPE | IgG | 23 MoM +++ | 9 MoM + | ≤ 4 MoM |
| | IgA | 3 MoM | 4 MoM + | ≤ 3 MoM |
| | IgM | 1 MoM | 1 MoM | ≤ 5 MoM |
| aPC | IgG | 1 MoM | 2 MoM | ≤ 4 MoM |
| | IgA | 2 MoM | 1 MoM | ≤ 3 MoM |
| | IgM | 1 MoM | 1 MoM | ≤ 4 MoM |

Figure 15

Lupus Anticoagulant Activity
Whole Blood Broth

|          | Immediate Mix 1:1 | Incubated Mix 1:1  1-2 hours |
|----------|-------------------|------------------------------|
| dRVVT    | 46.7 sec*         | 104.4 sec                    |
| dPT      | 42.5 sec†         | 48.7 sec                     |

\* normal = 28 - 49 sec   † normal = 29.6 - 41.8

Figure 16

Autoantibodies identified by Immunofluorescence

Observed fluorescence patterns on Hep-2 cell line

- Anti-nucleolar (scleroderma associated)
- Anti-lamins (very bright at nuclear pores)
- Anti-mitochondrial (cytoplasmic)
- Anti-centriole (unknown significance)

Figure 17

ANA Antibodies Identified by ImmunoConcepts Laboratories*

Using the RELISA® screening assay

| Sample | Units† |
|---|---|
| Cord serum | 0 |
| Cord stationary | 27 |
| Cord shake | 75 |
| ACS serum | 0 |
| ACS shake + heat | 90 |

*Sacramento, California   † < 10 units = neg   10-15 units = borderline

Figure 20

Reconstituted Lyophilized IvIg

Antiphospholipid Antibody (aPL) Results

|     |     | PL binding protein dependent | PL binding protein independent | Normal ranges |
|-----|-----|------------------------------|--------------------------------|---------------|
| aPS | IgG | 31 MoM +++                   | 4 MoM                          | ≤ 4 MoM       |
|     | IgA | 1 MoM                        | 1 MoM                          | ≤ 3 MoM       |
|     | IgM | 1 MoM                        | 1 MoM                          | ≤ 5 MoM       |
| aCL | IgG | 7 MoM +                      | 1 MoM                          | ≤ 4 MoM       |
|     | IgA | 1 MoM                        | 1 MoM                          | ≤ 4 MoM       |
|     | IgM | 1 MoM                        | 1 MoM                          | ≤ 6 MoM       |
| aPE | IgG | 32 MoM +++                   | 3 MoM                          | ≤ 4 MoM       |
|     | IgA | 1 MoM                        | 1 MoM                          | ≤ 3 MoM       |
|     | IgM | 1 MoM                        | 1 MoM                          | ≤ 5 MoM       |
| aPC | IgG | 5 MoM +                      | 1 MoM                          | ≤ 4 MoM       |
|     | IgA | 1 MoM                        | 1 MoM                          | ≤ 3 MoM       |
|     | IgM | 1 MoM                        | 1 MoM                          | ≤ 4 MoM       |

Figure 21

METHOD OF ALTERING THE BINDING SPECIFICITY OF PLASMA PROTEINS BY OXIDATION-REDUCTION

This application is a continuation of U.S. application Ser. No. 12/107,819 filed on Apr. 23, 2008, now U.S. Pat. No. 8,334,146, which is a continuation-in-part application of U.S. application Ser. No. 10/863,365, filed Jun. 9, 2004, now U.S. Pat. No. 7,368,542, which claims the benefit of the filing date of U.S. Provisional Application No. 60/476,607, filed Jun. 9, 2003. U.S. application Ser. No. 12/107,819 is also a continuation of application Ser. No. 11/359,489, filed Feb. 23, 2006, now U.S. Pat. No. 7,892,751, which is a continuation-in-part of U.S. patent application Ser. No. 11/108,826, filed on Apr. 19, 2005, which application is a continuation-in-part of Ser. No. 10/863,365, filed Jun. 9, 2004, now U.S. Pat. No. 7,368, 542, which application claims the benefit of U.S. Provisional Application Ser. No. 60/476,607, filed Jun. 9, 2003, the contents of each of which are incorporated by reference herein in their entireties.

FIELD OF INVENTION

The present invention relates to a method of altering a binding specificity of a plasma protein that has a binding specificity that can be altered by oxidation-reduction reactions. The present invention further relates to a method of obtaining autoantibodies by unmasking autoantibodies naturally present in the blood, plasma or serum of normal subjects.

BACKGROUND OF THE INVENTION

The term "autoimmune disease" refers to a group of diseases wherein the immune system mistakenly attacks cells, tissues and organs of a person's own body. Typically, autoimmune diseases involve antibody binding of the body's own components, such as common proteins and lipids. Antibodies that bind to self-compounds (or, more typically, to compounds that are so common that they are found in every organism) are referred to as autoantibodies. As an example, autoantibody binding of phospholipids and/or phospholipid-binding plasma proteins is associated with diseases such as systemic lupus erythematosus (SLE), deep vein and recurrent arterial thrombosis, pulmonary embolisms, recurrent spontaneous abortion, thrombocytopenia, chorea, epilepsy, livedo, idiopathic pulmonary hypertension, rheumatological conditions and a host of collagenous diseases. Other diseases associated with autoantibodies include multiple sclerosis, Crohn's disease, discoid lupus erythematosus, Hashimoto's thyroiditis, psoriasis, diabetes and rheumatoid arthritis. There are about 80 different autoimmune diseases, and as a group, these diseases affect millions of people.

A conventional theory regarding the etiology of autoimmune diseases has been that these diseases are caused by an overproduction of autoantibodies in the diseased individual, possibly due to an overexpression of a gene encoding such autoantibodies. According to this theory, the blood of an affected individual contains an elevated level of the particular autoantibody causing the disease, while the blood of a normal individual contains none of the autoantibody or only a trivial amount. This theory is seemingly supported by conventional assays, in which abundant autoantibodies can be detected in blood, or blood products such as plasma or serum, from subjects having an autoimmune disease, whereas only a zero or minimal amount of autoantibodies can be detected in blood or blood products from subjects that do not have an autoimmune disease.

The present invention is based on the remarkable discovery, reported herein, that blood from normal individuals in fact contains a significant number of autoantibodies, in a wide variety of types and specificities. It is possible to detect and isolate these autoantibodies from blood or a blood product of a normal individual if the blood or blood product is treated by oxidation, by, for example with an oxidizing agent or electric current, according to a method described herein. This discovery of autoantibodies in significant quantities in normal blood is previously unreported and, to the best of the inventor's knowledge, the existence of such autoantibodies in significant quantities in normal blood was completely unknown prior to the present invention.

Without being held to any particular theory, it is evident that if autoantibodies may be obtained by manipulating normal blood taken from persons who do not have any symptoms of autoimmune disease, then it must be that the immune system of normal persons routinely creates and circulates these autoantibodies, but in some form wherein they are masked or blocked, or otherwise prevented from having any harmful effects.

The discovery of autoantibodies in significant quantities in normal individuals raises the question of why the autoantibodies are not detected in a standard assay (typically based on the binding of an antibody to its corresponding antigen) and why the autoantibodies do not cause disease symptoms in normal individuals.

Based on earlier experiments described herein, a initial tentative explanation for how normal blood could contain autoantibodies without such antibodies being detected through ordinary screening procedures and without such antibodies causing disease, was that autoantibodies in normal individuals were somehow sequestered after they are produced. For example, the sequestration could be in the form of macromolecules such as a low or high-density lipoproteins (LDL, HDL) or some other type of microparticles, vesicles or micelles that could have the ability to keep autoantibodies cordoned off and separated from other components of the bloodstream. Under this theory, autoimmune disease could be triggered, not by the production of autoantibodies per se, but by the breakdown, disruption or lack of formation of the macromolecules, microparticles, vesicles or micelles sequestering the autoantibodies. This theory seemed supported by the initial experiments wherein autoantibodies were obtained from blood or serum samples after fairly drastic manipulation of the samples including shaking and heating.

In later experiments, described herein, however, it was shown that simpler methods of the invention, such as exposing blood or a blood product to an oxidizing agent or to a DC electric current, can be enough to obtain autoantibodies from normal blood, and that the process is reversible. Further, it was found that autoantibodies could be obtained by treating commercial IvIg products, which would be free of any type of macromolecular sequestering entity. Based on these experiments, a more likely theory for how normal blood could contain autoantibodies without such antibodies being detected through ordinary screening procedures and without such antibodies causing disease, is that the autoantibodies freely circulate along with other antibodies but that the antigen binding site of autoantibodies is somehow blocked or inactivated in normal individuals. Under this theory, autoimmune disease could be triggered by oxidation to unblock the antigen-binding site of autoantibodies. Further, this theory suggests a more general mechanism by which the binding specificity of certain plasma proteins may be altered.

An immediate practical use of the discovery that forms the basis of the present invention is that it allows for an almost unlimited supply of autoantibodies to be obtained, which autoantibodies can be used as standards in diagnostic kits for the laboratory diagnosis of autoimmune and other aPL-related diseases. Previously, collection of large amounts of autoantibodies for commercial use has been difficult because it was thought that the autoantibodies had to be obtained from individuals having an autoimmune disease or testing positive for autoantibodies in standard assays. The amount of such blood that can be obtained from phlebotomy of individual patients or by pooling blood from a group of patients known to test positive for autoantibodies is limited. Other methods of obtaining autoantibodies, such as screening phage libraries as described in U.S. Pat. No. 5,885,793, may be difficult and time-consuming.

Testing blood samples for the presence or absence of masked antibodies may have important diagnostic value as it might presage or predict what antibodies could appear subsequent to oxidative stress in particular individuals

SUMMARY OF THE INVENTION

It is the object of this invention to provide a method of altering a binding specificity of a plasma protein that has a binding specificity that can be altered by a change in its redox state.

It is a further object of the present invention to provide a method of obtaining autoantibodies from blood, plasma or serum from normal individuals.

It is a further object of the present invention to provide a method of treating a subject having an autoimmune disease by administering to the subject an antioxidant sufficient to inactivate autoantibodies in said subject.

It is a further object of the present invention to provide a method of treating a subject having an autoimmune disease by inactivating autoantibodies of said subject extracorporeally.

It is a further object of the present invention to provide a product comprising a biological fluid or a protein-containing extract of a biological fluid that has been exposed to an oxidizing agent or a DC electric current sufficient to alter the binding specificity of at least one protein contained therein.

It is a further object of the present invention to provide a blood, plasma or serum sample from one or more persons who test negative for the presence of autoantibodies in routine clinical assays and which has been treated so that the blood, plasma or serum subsequently demonstrate the presence of autoantibodies.

These and other objectives are achieved by a method of altering a binding specificity of at least one circulating protein in a biological fluid or in a protein-containing extract of a biological fluid, the circulating protein having a binding site with a binding specificity that can be altered by a change in a redox state of the protein, by exposing the protein in the biological fluid or extract to an oxidizing agent or to a direct electric current (DC) to effect the alteration of the binding specificity of the circulating protein.

The objects are further achieved by a method comprising the steps of providing a composition comprising at least one plasma protein suspended or dissolved in a liquid medium, the plasma protein having a binding specificity that can be altered by a change in its redox state, and exposing the composition to an oxidizing agent or a DC electric potential sufficient to effect the alteration of the binding specificity of the plasma protein.

In another embodiment, the invention relates to a method of obtaining autoantibodies or other masked circulating proteins from a biological fluid or from an extract of a biological fluid by exposing the autoantibody or other masked circulating protein in the biological fluid or extract to an oxidizing agent or to a DC electric current sufficient to alter the binding specificity of the autoantibody or other masked circulating protein so that the autoantibody or other masked circulating protein becomes capable of binding to an antigen or ligand, thereby becoming detectable and recoverable from the biological fluid or extract, and recovering the autoantibody or other masked circulating protein from the biological fluid.

In another embodiment, the present invention relates to a method of treating an autoimmune disease by administering to a subject having an autoimmune disease an amount of an antioxidant sufficient to inactivate autoantibodies in the subject. A treatment of a person having an autoimmune disease may include extracorporeal treatment of the blood to reduce the unmasked proteins and replace them as masked proteins.

In another embodiment, the present invention relates to a method of screening a normal individual's biological fluid or extract to determine which autoantibodies are masked and thus construct a potential antibody profile of autoantibodies that could cause autoimmune disease in that individual if exposed or unmasked by oxidation or an electromotive force.

As a particular, non-limiting example, blood, plasma or serum, or a blood extract such as an immunoglobulin mixture, may be exposed to an oxidizing agent or to a DC electric current to effect the alteration of the binding specificity of at least one autoantibody contained in the blood, plasma, serum or extract, so that the autoantibody becomes detectable in and recoverable from the blood, plasma, serum or extract.

BRIEF DESCRIPTION OF THE DRAWINGS

FIG. 1 is a table listing the particular antiphospholipid antibodies (aPL) that were assayed by the in-house enzyme-linked immunosorbent assay (ELISA) format used in many of the Examples, described below.

FIG. 2 is a table summarizing aPL assay results for a blood sample from a normal aPL-negative subject, incubated according to the method described in the opening section of the Examples.

FIG. 3 is a composite table summarizing aPL assay results of blood samples from seven aPL-negative normal individuals, incubated according to the method described in the opening section of the Examples.

FIG. 4 is a table summarizing aPL assay results for a serum sample from a normal aPL-negative subject, incubated according to the method described in the opening section of the Examples, with the feature that horse red blood cells (RBC) were substituted for human RBC in the procedure.

FIG. 5 is a table summarizing aPL assay results of an incubation of a serum sample carried out according to a method described in the opening section of the Examples, except that horse serum was substituted for human serum.

FIG. 6 is a table summarizing aPL assay results for a blood sample from a normal aPL-negative subject, incubated according to the method described in the opening section of the Examples, except that the incubation was carried out at room temperature (22° C.).

FIG. 7 is a table summarizing aPL assay results for a blood sample from a normal aPL-negative subject, incubated according to the method described in the opening section of the Examples, with the feature that 0.7 mm Degalan (plastic) beads were used as the particulate solid in the incubation mixture.

FIG. 8 is a table summarizing aPL assay results for a blood sample from a normal aPL-negative subject, incubated according to the method described in the opening section of the Examples, except that the incubation mixture was kept stationary, instead of being shaken or rocked.

FIG. 9 is a table summarizing aPL assay results for a blood sample from a normal aPL-negative subject, incubated according to the method described in the opening section of the Examples, with the added feature that the incubation mixture was heated to 56° C. for 30 minutes.

FIG. 10 is a table summarizing aPL assay results for a blood sample from a normal aPL-negative subject, incubated according to the method described in the opening section of the Examples, with the feature that a bacterial culture growth medium from a different supplier (Becton Dickinson, Sparks, Md.) was used in place of the bacterial culture growth medium from Biomerieux.

FIG. 11 is a table summarizing aPL assay results for a blood sample from a normal aPL-negative subject, incubated according to the method described in the opening section of the Examples, with the feature that the incubation occurred under anaerobic conditions.

FIG. 12 is a table summarizing aPL assay results for a blood sample from a normal aPL-negative subject, incubated according to the method described in the opening section of the Examples, with the feature that K562 cells (a human tumor cell line) were used instead of RBC.

FIG. 13 is a table summarizing aPL assay results for a blood sample from a normal aPL-negative subject, except that the bacteria culture growth medium was replaced with a cell culture medium used for growing human cells.

FIG. 14 is a table summarizing aPL assay results for a cord blood sample from a normal aPL-negative mother and baby.

FIG. 15 is a table summarizing aPL assay results for a blood sample from a normal aPL-negative subject, incubated according to the method described in the opening section of the Examples, with the feature that sodium nitroprusside (SNP) was used in place of RBC in the incubation mixture.

FIG. 16 is a table summarizing results of a lupus anticoagulant activity assay for a blood sample incubated according to the method described in the opening section of the Examples. The blood sample was obtained from a subject whose blood is lupus anticoagulant negative prior to seroconversion by the present invention process.

FIG. 17 is a table listing other types of autoantibodies that have been identified in blood samples that are incubated according to the method described in the opening section of the Examples. The listed antibodies were identified by immunofluorescence microscopy.

FIGS. 19 A-D are flow cytometry histograms showing monocyte activity of various sera. In the histograms, antibody activity, if present, is measured by shifts in the median channel values (log scale) along the horizontal axis.

FIG. 20 is a table summarizing the results of anti-nuclear-antibody (ANA) testing of various samples using a RELISA® screening assay.

FIG. 21 is a table summarizing aPL assay results for a sample of lvlg that was incubated with hemin in a tris buffer.

DETAILED DESCRIPTION OF THE INVENTION

Figure 18:
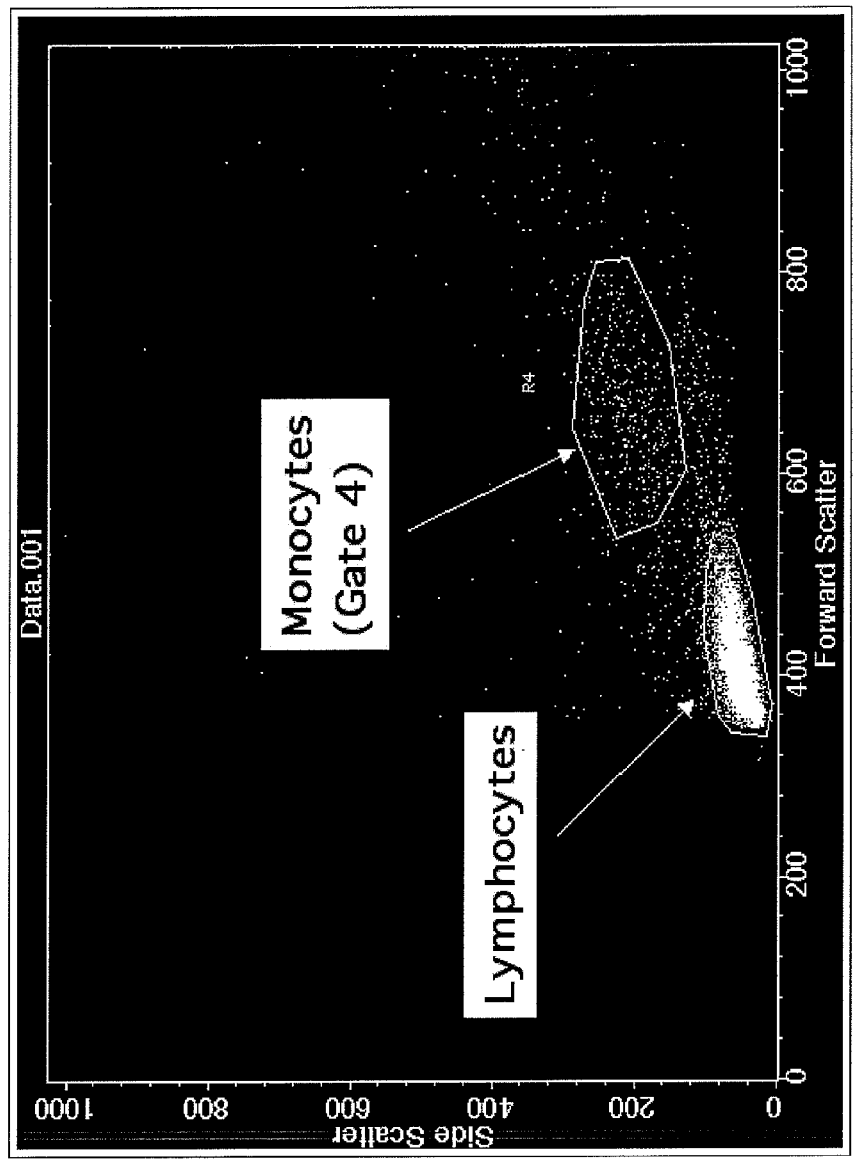
FIG. 18 is a graph showing the forward scatter (size) and side scatter (granularity) profile of the monocyte population of cells as defined for density gradient isolated human white blood cells by flow cytometry.

The present invention relates to a method of altering the binding specificity of at least one plasma protein or circulating protein in a biological fluid or extract of a biological fluid. As used herein, the terms "circulating protein" and "plasma protein" are used to refer to a protein naturally found in the circulation system of animals. Examples of circulating proteins include antibodies and other plasma proteins. It is to be understood that the method of the invention is not meant to apply universally to all plasma proteins or circulating proteins, but rather applies to any plasma protein or circulating protein that has the property of having a binding specificity that can be altered by a change in the redox state of the protein. The discovery by the inventor that there are circulating proteins, such as autoantibodies, that have this property forms a basis of the invention. Examples of non-antibody proteins that have been found to have a binding specificity that can be altered by a change in the redox state include kininogen and prothrombin and/or beta2 glycoprotein.

The term "masked circulating protein" is newly coined for the present invention to designate and describe a circulating protein that, in normal individuals, is present in the blood, but is not detectable by conventional binding assays based on receptor-ligand binding because its binding site is, in the normal individual or in a sample taken from the normal individual, masked or blocked or otherwise prevented from binding an antigen, and that, when a sample containing the masked circulating protein is treated by changing its redox state, such as by exposure to an oxidizing agent or electric current according to a method of the present invention, becomes capable of binding an antigen and thereby becomes detectable in a sample. An example of a masked circulating protein is an autoantibody. As discovered by the present inventor, autoantibodies circulate in significant quantities in normal blood, but they are not detectable in conventional assays based on antibody-antigen binding. As discussed herein, an autoantibody becomes detectable and recoverable when the autoantibody is subjected to oxidation-reduction conditions sufficient to alter its binding specificity. Autoantibodies that have been unmasked by oxidation include anti-phospholipid, anti-nucleolar (scleroderma associated), anti-lamins (very bright at nuclear pores), anti-mitochondrial (cytoplasmic), and anti-centriole antibodies. Further, it has also been found that blood, serum or lvlg samples that initially test negative for HCV (hepatitis C virus) tests positive for HCV after a treatment according to the present invention, suggesting that normal individuals have masked anti-HCV antibodies in their circulation.

The term "altering the binding specificity" of a protein refers to a process whereby a protein is changed or altered, such as by oxidation or reduction, so that it becomes capable of specific binding of an antigen or ligand that it had not previously been capable of specifically binding or becomes incapable of specific binding of an antigen or ligand that it had previously been capable of specifically binding. The term "unmasking" refers to a process wherein the binding specificity of a masked circulating protein is altered so that the protein becomes detectable by a binding assay based on the altered binding specificity.

The term "autoantibody" refers to any naturally occurring antibody produced by the immune system of an animal and that binds to a self-antigen, that is, to a compound or antigen produced by the animal itself.

The term "biological fluid" includes any bodily fluid that contains circulating proteins, including plasma, serum and whole blood, saliva, urine, lactation fluids and other secretions. The term "protein-containing extract of a biological fluid" refers to any preparation that is collected or separated from a biological fluid, such as immunoglobulin fractions. Blood, serum or plasma that may be used in the present invention may be freshly obtained from an individual, or it may be obtained from such sources as pooled blood or plasma preparations obtained from blood banks or other blood collection facilities. For the purposes of the present invention, the blood, serum or plasma may also be from collections that are out-of-date or otherwise found to be substandard by blood banks or blood collection facilities. Although this description focuses upon human blood, plasma and serum, the identical process of this invention can be applied to animal blood and should result in obtaining analogous animal antibodies for purposes relating to veterinary medicine. Preferably, blood or serum used in the method of the invention is diluted to reduce the effect of any antioxidants that may be contained in the blood, plasma or serum.

In the method of the present invention, the binding specificity of at least one circulating protein or plasma protein in a biological fluid is altered by exposing the protein to an oxidant or to an electric current. For example, the binding specificity of a masked circulating protein can by altered so that the protein is unmasked, that is, so that it is able to bind an antigen that it was not able to bind before the method was carried out. A protein that has had its binding specificity altered may then be isolated and recovered by any separation method based on specific binding.

If an oxidizing agent is used to carry out the method of the invention, the oxidizing agent can be any compound that is capable of altering the redox state of a biological molecule. More specifically, the oxidizing agent is a molecule that has the ability to be reduced by acting as an electron acceptor for other molecules that act as electron donors. Examples of oxidizing agents include, but are not limited to hemin, chlorophyll, or other ring compounds containing a strong oxidizing metal, and $KMnO_4$. Typically, when an oxidizing agent is used, a mixture of the biological fluid or extract and the oxidizing agent must be incubated for a period of time, typically for about a day or overnight. The oxidizing agent should be used at a concentration sufficient enough to alter the binding specificity of a protein having an alterable binding specificity, but not at a concentration that might destroy the protein. In the case of autoantibodies, it has been found that different types of autoantibodies can interact differently with different antioxidants. For example, for the unmasking of aPC autoantibodies, the results are poor with hemin and very good with $KMnO_4$.

If a DC electric current is used to carry out the method of the invention, the method may be carried out by any means of delivering an electric current, such as by immersing positive and negative electrodes into a conductive solution containing the sample to be treated. Typically, a solution containing a biological fluid may be exposed to an electric potential of a sufficient magnitude and of a sufficient duration to alter the binding specificity of a protein having an alterable binding specificity. It has been found that positive results may be obtained by exposing a solution to an electric potential of 6-24 volts for a few seconds to a few minutes. As discussed in the examples, an extended exposure to an electric current may result in reversibility of the alteration of the binding specificity.

Attempts to produce positive results using an AC current have been unsuccessful.

Without being bound to a specific theory, it is preferred, in the case of an autoantibody, that the autoantibody be exposed to the oxidizing agent or electric current in an amount or for a time sufficient to oxidize an antigen binding site in a Fab portion of the autoantibody.

Whether a particular protein of interest is one that has a binding specificity that can be altered by changing its redox state and the effectiveness of any set of conditions for altering the binding specificity of the particular protein of interest may be readily determined by ELISA or other ligand-receptor assays. Such assays can be carried out before and after a protein is subjected to redox conditions to see whether the process has altered the binding specificity of the protein. For example, the best oxidizing agent to recover a specific autoantibody can be readily determined by simple experimentation.

A further aspect of the present invention is the possibility of treating a subject having an autoimmune disease, either by administering to the subject an amount of an antioxidant sufficient to inactivate autoantibodies in the subject or by taking a blood sample from the subject, exposing the blood sample to an antioxidant or electric current sufficient to inactivate autoantibodies in said blood sample, and returning the blood sample to the subject.

A further aspect of the present invention is a method of screening a normal individual's biological fluid or extract to determine which autoantibodies are masked and thus construct a potential antibody profile of autoantibodies that could cause autoimmune disease in that individual if exposed or unmasked by oxidation or an electromotive force. For example, in general terms, a blood, plasma or serum sample from a subject can be assayed to determine an amount and/or type of autoantibodies detectable in the sample. Thereafter, a blood, plasma or serum sample from the subject can be treated by exposing the sample to an oxidizing agent or a DC electric current, and the treated blood, plasma or serum sample from the subject can be assayed to determine an amount and/or type of autoantibodies detectable in the treated sample. Thereafter, the amount and/or type of autoantibodies detectable in the sample before the treating step can be compared with the amount and/or type of autoantibodies detectable in the sample after the treating step.

It has been found that untreated blood, plasma, serum or lvlg samples and blood, plasma or serum or lvlg samples treated according to the method of the present invention can be lyophilized and shipped or stored. When the samples are reconstituted, they retain their respective activity.

EXAMPLES

Having described the invention, the following examples are given to illustrate specific applications of the invention, including the best mode now known to perform the invention. The examples are presented in approximate chronological order and thus show a progression in the understanding of components and procedures required to achieve the effects of the invention. These specific examples are not intended to limit the scope of the invention described in this application.

Regarding each of the Examples 1-17 described herein, unless otherwise noted, the following procedure was typically used: A 10 ml sample of whole blood or 5 ml of serum or plasma from a normal aPL-negative subject and 4-5 ml of packed mammalian red blood cells were added to a vial containing 30 ml of Biomerieux brand bacterial culture growth medium (containing at least the following ingredients: distilled water, soybean-casein digest broth, yeast extract; dextrose; sucrose; hemin; menadione (vitamin K3); pyridoxal HCl (vitamin B6); and sodium polyanetholesulfonate (SPS) and charcoal. Then, the mixture was incubated, with rocking or shaking, at 37° C. for a period of 18-22 hours. Following the incubation and centrifugation, a sample of the incubated blood or serum/RBC was tested for the presence of antiphospholipid antibodies (aPL) using a comprehensive in-house ELISA aPL format that provides 24 separate aPL test results. The testing procedure is described in greater detail in the following publications, incorporated herein by reference: Wagenknecht D R, et al., The Evolution, Evaluation and Interpretation of Antiphospholipid Antibody Assays, Clinical Immunology Newsletter, Vol. 15, No. 2/3 (1995) pp. 28-38 and McIntyre J A, et al., Frequency and Specificities of Antiphospholipid Antibodies (aPL) in Volunteer Blood Donors, Immunobiology 207(1): 59-63, 2003.

FIG. 1 shows the 24 separate aPL specificities that were tested for by using the comprehensive in-house ELISA aPL format. Four specificities were assessed, 1) aPS=antiphosphatidylserine, 2) aCL=anticardiolipin, 3) aPE=antiphosphatidylethanolamine, and 4) aPC=antiphosphatidylcholine. For each of these aPL specificities, three immunoglobulin isotypes were sought, IgG, IgA and IgM. Each specificity and each isotype were assessed in the presence (dependent) and absence (independent) of a buffer diluent supplement, 10% adult bovine plasma (ABP), which contains the phospholipid-binding plasma proteins) or 1% bovine serum albumin, (BSA, which is devoid of phospholipid-binding plasma proteins), respectively. The final dilution of the subjects' blood samples was between 1/50 and 1/100.

The results in the 24 aPL specificities obtained for the various experiments described herein are given in the accompanying figures. The positive/negative findings are expressed in multiples of the means (MoM) based on testing plasma samples from 775 normal blood donors, as described in McIntyre J A, Immunobiology, above. The presence of +++ indicates strong antibody activity. The markers of + and ++ indicate low and intermediate antibody activity, respectively. The figures also provide the normal range values for each aPL specificity and isotype combination.

A positive result in the column indicated as PL binding protein "dependent" means that the antiphospholipid antibody (aPL) is actually binding to a plasma protein that initially has bound to the particular phospholipid indicated. Plasma proteins that typically can be bound by PS and CL include the following: $beta_2$-glycoprotein I, prothrombin, protein C, protein S, annexin V, and complement components Factor H and C4 (see, for example, McIntyre, J. A., Wagenknecht, D. R. and Faulk, W. P. Antiphospholipid antibodies: Discovery, definition, detection and disease. Prog. Lipid Res. 42(3): 176-237, at page 182). The physiological nature of the plasma protein binding is not known precisely for all of the phospholipids, but such binding is thought to induce conformational changes in the plasma protein structure, thereby exposing novel or cryptic epitopes that then are targeted by the individuals' autoantibodies. Plasma proteins that typically can be bound by phospholipid PE include the following: high and low molecular weight kininogens, and factor XI and prekallikrein. The latter two proteins can be detected by virtue of their fidelity in binding to high molecular weight kininogen. The plasma proteins that bind to PC have not yet been defined. In certain experiments, plasma-protein independent aPL are observed (see FIG. 3). A possible explanation for this activity is that it represents the presence of residual phospholipid-binding plasma proteins that are present in the original blood sample.

Example 1

A sample of blood from a normal subject was incubated and tested according to the procedure described above. The results of the aPL ELISA are shown in FIG. 2. As shown in FIG. 2, the incubated blood sample shows a dramatic presence of autoantibody activity, in comparison to the normal, untreated blood shown in the Normal ranges column. In particular, strong autoantibody activity is shown in the protein-dependent category for aPS (IgG), aCL (all isotypes), and aPE (IgG). The low or absent IgG aPC autoantibody activity was a characteristic finding in the early examples and in procedures in which hemin was used as the oxidizing agent. This result indicates that autoantibodies to PC, especially of the IgG isotype are different and perhaps do not become activated in the same way as do the others. In later experiments, it was found that significant levels of aPC can be detected in samples that were treated with $KMnO_4$ (data not shown).

Example 2

Blood samples drawn from seven healthy subjects were incubated and tested according to the procedure described above. In particular, all seven subjects' bloods were drawn within a 20 minute period and incubated for 20 hours in identical conditions. FIG. 3 is a composite table showing the range of aPL seroconversion for these seven samples. These results show that there are variations in the aPL levels detected as well as the isotypes present among different individuals. Nevertheless, as shown by the invention, each individual had aPL antibodies that could be detected after incubation.

Example 3

In a first experiment, a serum sample from a normal subject was incubated and tested according to the basic procedure described above. In the incubation mixture, horse red blood cells (RBC) were used instead of human RBC. The results of the aPL ELISA are shown in FIG. 4. As shown in FIG. 4, significant aPL activity was obtained, particularly with respect to aPS (IgG and IgM) and aCL (IgA and IgM).

In a second experiment, a horse serum, instead of human serum, was incubated with human RBC and tested according to the basic procedure described above. The results of the aPL ELISA are shown in FIG. 5. As shown in FIG. 5, aPL activity was not obtained. (The ELISA assay used in this experiment utilized human-antibody-specific alkaline phosphatase labeled antibody probes to detect aPL, so whether the incubated sample contained horse aPL is unknown.)

The results shown summarized in FIGS. 4 and 5 unequivocally demonstrate that all aPL that are obtained during the seroconversion process of the present invention originate from the human serum and are not released from the human RBC, since the first experiment uses horse RBC, which are devoid of human antibodies, in place of human RBC and still shows positive results, whereas the second experiment uses horse serum in the presence of human RBC and shows negative results.

Example 4

A blood sample from a normal subject was incubated and tested according to the basic procedure described above, except that the incubation was carried out at room temperature (22° C.), instead of at an elevated temperature. FIG. 6 shows that the sample did not undergo seroconversion when incubated at room temperature. These results suggest that the process of seroconversion may be temperature sensitive.

Example 5

A blood sample from a normal subject was incubated and tested according to the basic procedure described above, with the feature that 0.7 mm Degalan (plastic) beads were used as the particulate solid in the incubation mixture instead of charcoal. Since charcoal was used in initial experiments showing seroconversion, this experiment was carried out to determine whether charcoal plays a specific role in the seroconversion. FIG. 7 shows that the sample exhibited seroconversion even when plastic beads were used in place of charcoal. These results suggest that the role of charcoal is mechanical, rather than chemical, in nature, and that any particulate solid, such as plastic, resin or glass beads, can be used. Without being limited to any particular theory, it can be theorized that the particulate component acts as an abrasive upon the RBC membrane, probably causing release of the NO ion from the RBC, either by interacting with the RBC AE1/Band 3 protein or with the SNO-hemoglobin transition molecules or both. The possibility of mechanical abrasion is supported by the observation in Example 6, wherein negative assay results are shown for an incubation mixture that is not rocked or shaken. The particulate solids may also serve a mechanical function of assisting autoantibody release.

Example 6

A blood sample from a normal subject was incubated and tested according to the basic procedure described above except that the incubation mixture was kept stationary, instead of being shaken or rocked. FIG. 8 shows that the sample did not undergo seroconversion when it was kept stationary. These results suggest that movement may facilitate interaction between solid particles and RBC. Stationary incubation conditions did not facilitate aPL release, although a small amount of movement such as produced by transport of the samples to the incubator may produce small amounts of aPL release.

Example 7

A blood sample from a normal subject was incubated and tested according to the basic procedure described above, with the added feature that after incubation and removal of RBC and charcoal by centrifugation, the incubation mixture was heated to 56° C. for 30 minutes. FIG. 9 shows that the amount of detected aPL was significantly increased by this procedure.

Example 8

A blood sample from a normal subject was incubated and tested according to the basic procedure described above, with the feature that a bacterial culture growth medium from a different supplier (Becton Dickinson, Sparks, Md.) was used in place of the bacterial culture growth medium from Biomerieux. FIG. 10 shows that the sample exhibited seroconversion in the Becton Dickinson medium, indicating that the method of the present invention is not dependent upon a bacterial culture growth medium from a particular source.

Example 9

A blood sample from a normal subject was incubated and tested according to the basic procedure described above, with the feature that the incubation occurred under anaerobic conditions (under nitrogen) instead of under aerobic conditions (in the presence of oxygen and $CO_2$). FIG. 11 shows that the sample exhibited seroconversion even under anaerobic conditions and that the method of the present invention is not dependent upon an aerobic environment.

Example 10

A blood sample from a normal subject was incubated and tested according to the basic procedure described above, with the feature that K562 cells (a human hematopoetic tumor cell line) were used instead of red blood cells. Further, only 11.3 million K562 cells were present in the culture media, compared to 3-4 mls of packed RBC typically used in the method of the invention. FIG. 12 shows that the sample exhibited seroconversion.

Other experiments have shown that samples that are incubated with other isolated cell types, lymphocytes, monocytes and neutrophils typically do not exhibit aPL seroconversion. In particular, white blood cells of the lymphoid and myeloid series did not support aPL release, nor did a cell line of porcine B lymphocytes designated as L14 (data not shown). These results suggest that hemoglobin may be a key component in the incubation mixture, since K562 cells and RBC contain hemoglobin, and lymphocytes, monocytes and neutrophils do not.

Example 11

A blood sample from a normal subject was incubated and tested according to the basic procedure described above, except that the bacteria culture growth medium was replaced with a cell culture medium used for growing human cells: RPMI. FIG. 13 shows that seroconversion did not occur. This experiment shows the importance of some ingredient in the bacterial culture media for the purpose of this invention. While RPMI is a culture media designed for human cells, it does not support aPL release when substituted for vial broth. Listings and comparisons of the ingredients in the two different microbiology vial broths with RPMI show that RPMI lacks hemin and menadione (a man-made provitamin K) called vitamin K3. It is known that hemin is a porphyrin chelater of iron (Fe+++) derived from RBC, and menadione is a fat-soluble vitamin. This indicates that redox reactions may play a role in autoantibody release Example 12

A placental cord blood sample incubated and tested according to the basic procedure described above. The placental cord blood was drawn after the birth of the baby, but before the placenta was detached from the uterine wall. Neither the mother's blood nor the baby's cord blood showed the presence of aPL in conventional laboratory assays. When processed according to the invention described herein, strong aPL antibody was demonstrated present in the cord blood samples, as shown in FIG. 14. The antibodies were IgG only, an observation that is compatible with antibodies of maternal origin. Since the mother transports IgG to the fetus prior to birth, this experiment seems to indicate that the masked maternal autoantibodies transported to the fetus by way of specialized FCγ receptors on the trophoblast (FcγRn) remain masked by the fetus in the fetal blood. Since the mother's blood and the cord blood were shown to be aPL-negative prior to seroconversion by the method of the invention, and since there were no IgM or IgA immunoglobulins detected, these findings support the contention that the IgG aPL observed in the cord blood subsequent to seroconversion are maternal in origin. It also is of interest that the trophoblast that expresses the FcγRn does not express HLA antigens.

Example 13

A plasma sample from a normal subject was incubated and tested according to the basic procedure described above; with the feature that sodium nitroprusside (SNP, 200 micromolar) was used in place of RBC in the incubation mixture. FIG. 15 shows that the sample exhibited seroconversion.

Since SNP is a potent nitric oxide (NO) donor, these results provide supportive evidence that the NO radical is involved in the autoantibody release and further support a theory that RBC and solid particulates fulfill a role of providing $NO^-$ donation from the RBC. Other free radical mediated reactions apart from sodium nitroprusside may also cause autoantibody release.

Example 14

A blood sample from a normal subject was incubated according to the basic procedure described above and was tested for lupus anticoagulant activity. Lupus anticoagulant or inhibitor is another type of aPL and is typically detectable only by functional laboratory assays. The results in FIG. 16 show a strong lupus anticoagulant (LA) in the seroconverted blood taken from a lupus inhibitor negative individual and processed by the method of this invention. While initially corrected by adding normal plasma to the seroconverted broth in the dRVVT assay, incubation for 1-2 hours resulted in the reappearance of the inhibitor. This time frame is proposed as the time it takes for the LA or unmasked antibodies to bind the relevant phospholipid-binding plasma proteins introduced by the mixing study. It also rules out the possibility of clotting factor deficiencies since a 1:1 mix provides sufficient levels of clotting factors to correct clotting times in a factor deficient sample. The dilute prothrombin time (dPT) did not correct in the presence of normal plasma and increased prolongation of clotting times was observed after incubation with normal plasma, which is indicative of a strong lupus inhibitor.

Example 15

Blood samples from five normal subjects were incubated according to the basic procedure described above and were tested by fluorescence microscopy for the presence of other types of autoantibodies. Sera and plasma samples from these five individuals were negative prior to processing according to the teachings of the invention. FIG. 17 lists additional autoantibody specificities identified by using the Hep-2 cell line. Identified were anti-nucleolar (scleroderma associated), anti-lamins (very bright at nuclear pores), anti-mitochondrial (cytoplasmic), and anti-centriole. The results show that autoantibodies released by the method of the present invention can also be detected by a different methodology of detection, fluorescence microscopy, as opposed to ELISA-based testing. The results confirm that many types of autoantibodies besides aPL are masked in the blood of individuals whose serum and plasma test negative for these antibodies in routine laboratory analyses.

From these results, it can be expected that many more autoantibody specificities await to be found by testing bloods processed by this invention.

Example 16

Figure 19A:
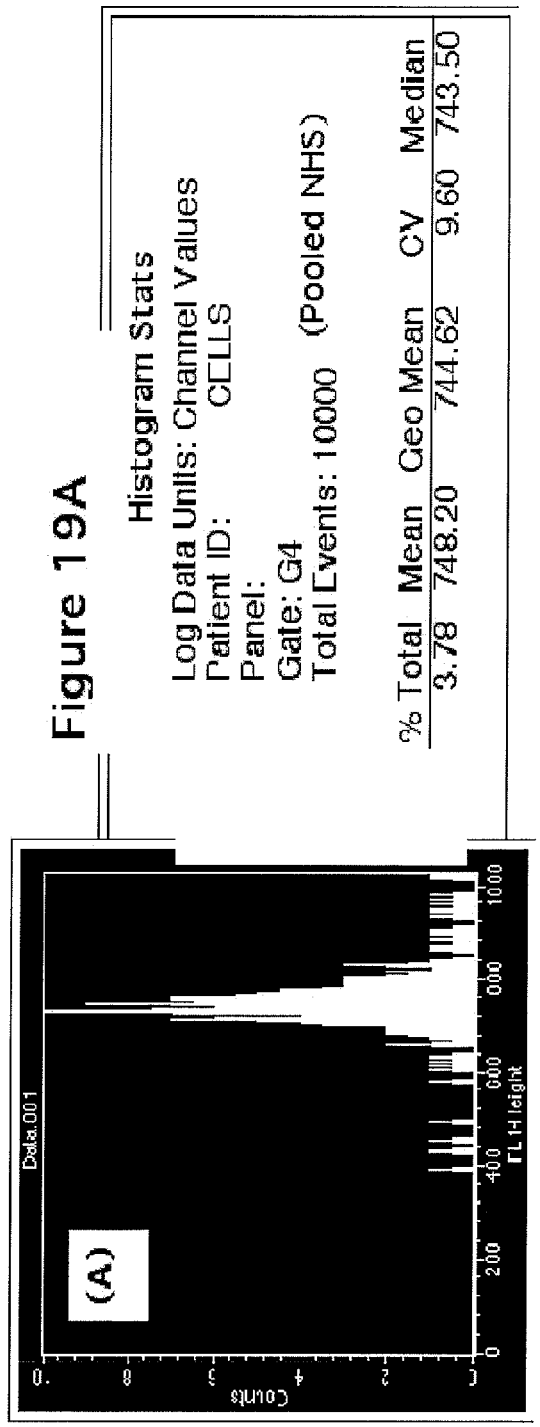
FIG. 19A shows monocyte reactivity of pooled normal human sera (NHS).
Figure 19B:
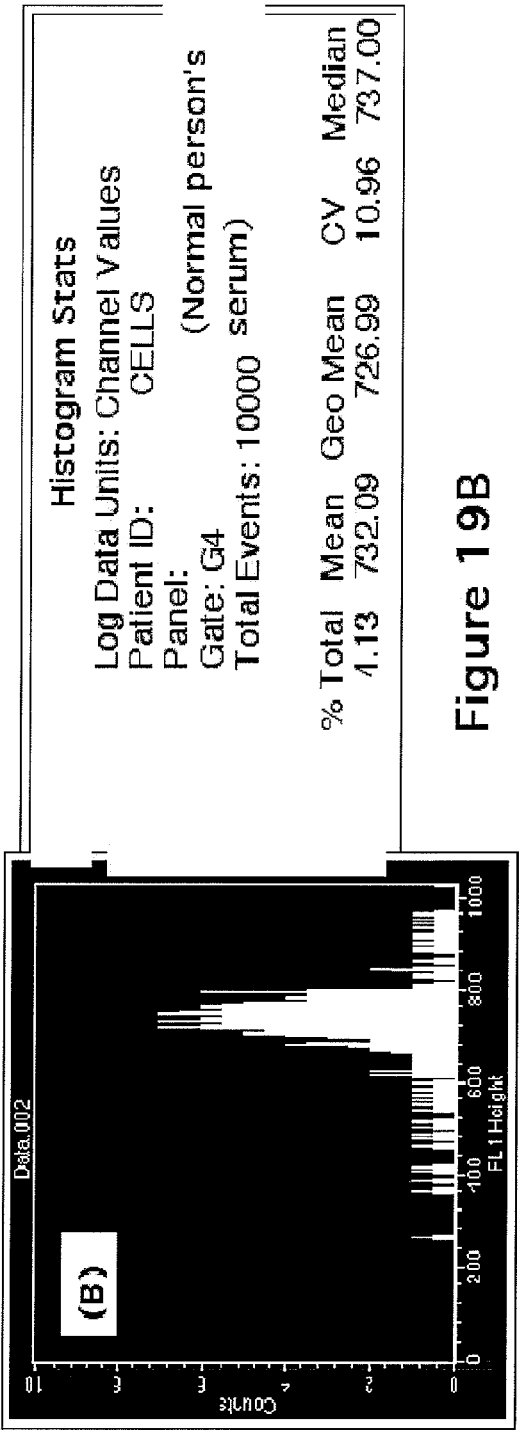
FIG. 19B shows the monocyte activity of a serum from a single normal subject.
Figure 19C:
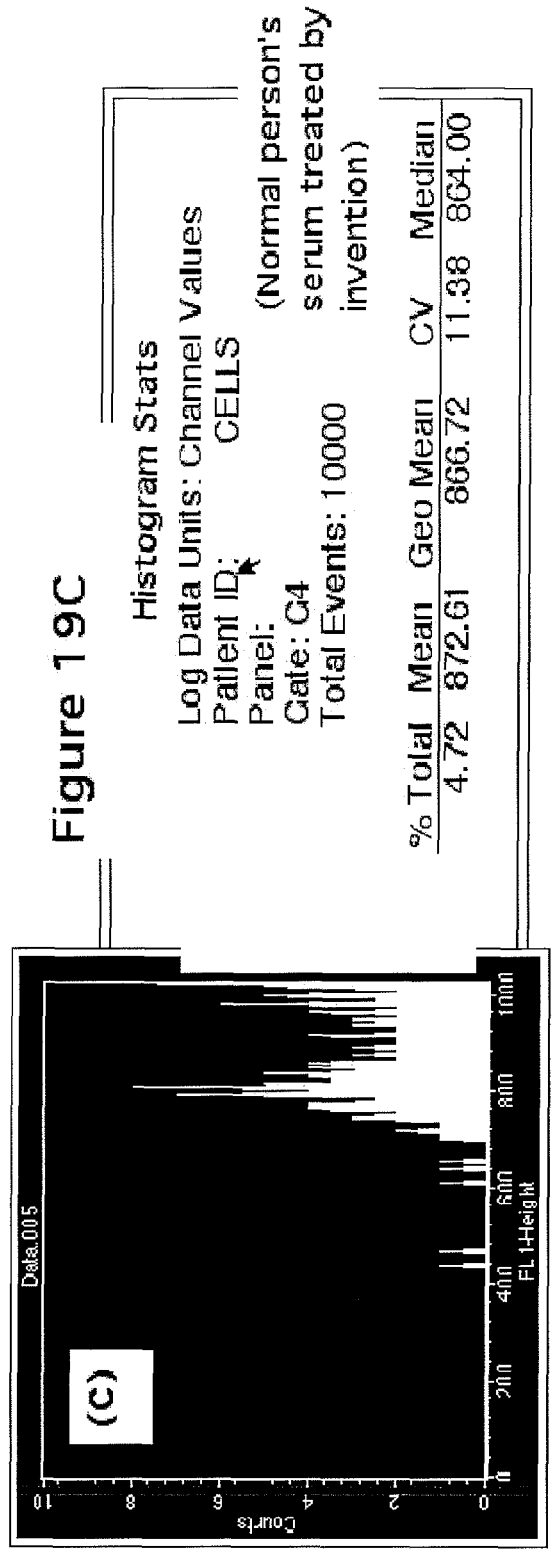
FIG. 19C shows the monocyte activity of a blood sample from the subject shown in FIG. 19B that was treated according to the method described in the opening section of the Examples.
Figure 19D:
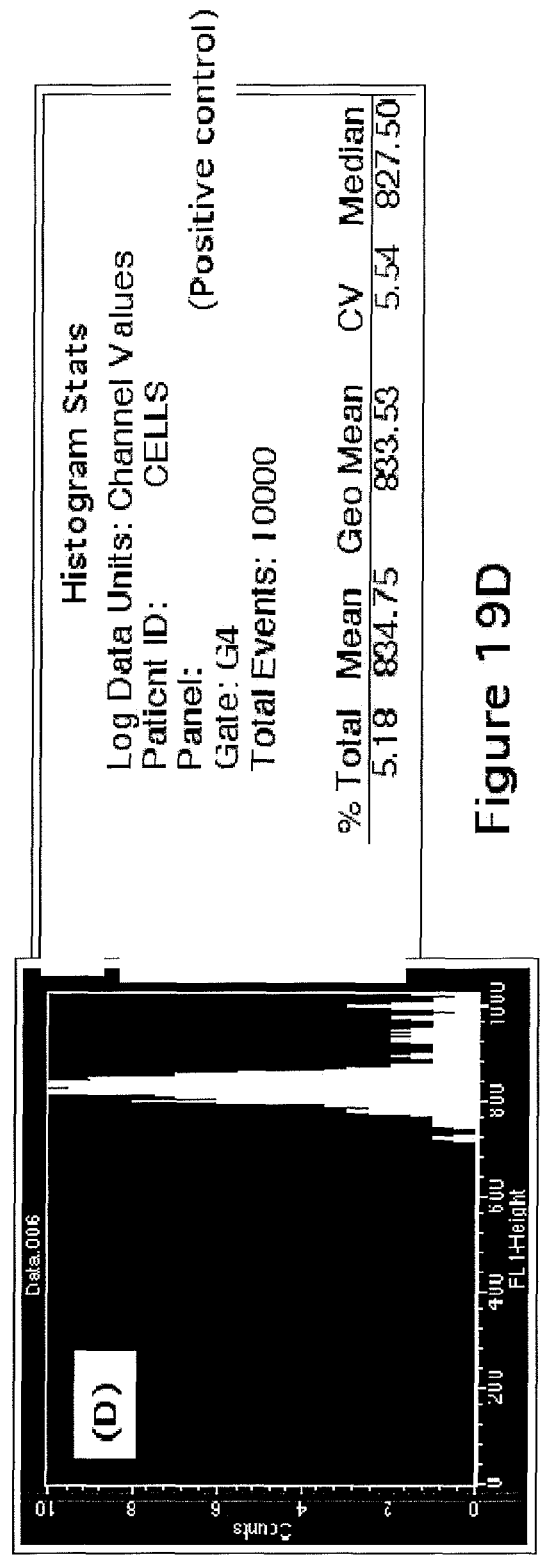
FIG. 19D shows the monocyte activity of positive control sera.

A blood sample from a normal subject was incubated according to the basic procedure described above and was tested for reactivity with monocytes using flow cytometry and fluorescent conjugated antihuman IgG antibodies. Comparative testing was done with untreated-pooled normal human sera (NHS), with serum from the same normal subject used with the invention and with positive control human sera. (The treated blood showed no auto reactivity with lymphocytes and neutrophils; these data are not shown.) FIG. 18 depicts the forward scatter (size) and side scatter (granularity) profile of the normal subject's monocyte population of cells as defined by flow cytometry. This monocyte population of cells was confirmed by showing reactivity with CD 14 monoclonal antibodies. FIG. 19A shows anti-monocyte reactivity with NHS. The median reactivity shown is 743.50 on a linear scale. FIG. 19B shows the auto-anti-monocyte activity of the normal subject's serum; this subject does not have antibody activity to autologous monocytes. The median reactivity shown is 737.00. FIG. 19C shows the auto-anti-monocyte activity of a blood sample from the subject shown in FIG. 19B after it is treated according to the method of the invention. The median value is shown is 864.00, indicating strong auto-anti-monocyte activity. Despite the fact that the plasma processed according to the teachings of the invention were used at a dilution of ⅛, it showed more reactivity with monocytes than did the undiluted positive control sera. Thus, this example shows that blood or serum samples processed according to the method of this invention release autoantibodies that specifically target monocytes. The same results were documented for four additional samples from other individuals when processed according to the teachings of the invention.

Example 17

Comparative tests for the presence of anti-nuclear-antibodies (ANA) using a RELISA® screening assay were carried out on untreated cord blood serum; cord blood incubated according to the method of the present invention, with no rocking; cord blood treated according to the method of the present invention, with rocking; untreated serum from an ANA-negative healthy donor (identified as ACS) and serum from the same ANA-negative healthy donor that was incubated according to the method of the present invention. As shown in FIG. 20, a significant amount of ANA was identified in cord blood and serum samples that were treated by the method of the present invention. From the results in FIGS. 16 and 17, it can be expected that many more autoantibody specificities wait to be found by testing bloods processed by this invention.

Example 18

To understand the role of red blood cells in the phenomenon of autoantibody release, experiments were designed to replace the red blood cells with simpler ingredients that might mimic the action of the red blood cells. In the present experiment, the red blood cells and charcoal were replaced with sodium nitroprusside (SNP) and ferric chloride. This substitution was made because sodium nitroprusside is a powerful nitric oxide producer, and it is known that the RBC are carriers of $NO^-$. Ferric chloride ($FeCl_3$ stock solution, 25 uM), was added as a substitute for the iron in hemoglobin.

Culture bottles containing the bacterial culture growth medium and 5 ml of human plasma or serum and varying concentrations of sodium nitroprusside (SNP, 200 μm) and exogenous ferric chloride (4.1 μm final concentration) was used in place of red blood cells and charcoal, were incubated at 37° C. and then heated to 56° C. for 30 minutes. The samples showed seroconversion of aPL, but only IgG (data not shown).

The results suggest that $NO^-$ may be involved in antibody unmasking, and suggest that the mechanical action of a solid phase material in the culture bottle disrupts the red blood cells and releases $NO^-$. Alternatively, the release or modification of NO may enable the hemoglobin molecule to participate in redox reactions.

Example 19

In an effort to determine whether the effect of unmasking autoantibodies was due to the breakdown of autoantibody-containing macromolecular structures within serum or blood or whether it was due to direct changes in the binding specificity of antibodies themselves, a series of experiments were carried out in which commercial intravenous immunoglobulin (Ivlg) was substituted for human plasma or serum. Commercial Ivlg is an alcohol precipitate fraction of pooled plasma from multiple donors, typically from 1,000-10,000 donors. Typically, Ivlg contains primarily IgG, and is mostly devoid of IgA, IgM and other plasma proteins. When untreated Ivlg is tested for the presence of autoantibodies by ELISA testing, the test results are negative. Because of its manner of preparation, Ivlg is also free of lipoprotein micelles, vesicles or other macromolecular structures. Therefore, if Ivlg were to test positive for the presence of autoantibodies after an incubation treatment, it would have to be that the autoantibodies were obtained by an alteration of IgG antibodies already present in the Ivlg preparation and not by a breakdown of structures or vesicles concealing the autoantibodies.

In the examples that follow, the commercial preparation of Ivlg used was lyophilized Ivlg (Immune Globulin Intravenous (Human) Gammar-P I. V., Aventis Behring, Kankakee, Ill.).

A 5 gram commercial preparation of lyophilized Ivlg was reconstituted in sterile phosphate buffered saline (PBS, 100 mg/ml). 1.7 ml of the reconsitituted Ivlg solution was added to a culture bottle containing the bacterial culture growth medium (without red blood cells or charcoal) and was incubated at 37° C. for 20 hours. The incubated mixture showed seroconversion and the presence of aPL IgG (data not shown). (As expected, only IgG was detected, not IgA or IgM.)

In similar experiments, autoantibodies were detected in a mixture that was incubated at room temperature in a shaking vial, but the results were not as good as at 37 degrees (results not shown).

Heating the Ivlg-bacterial growth medium mixture above 37° C. did not result in further increases in autoantibodies.

As a control, Ivlg straight out of the bottle was tested for aPL and other autoantibodies, and the results were negative.

Example 20

In Example 19, it is shown that autoantibodies can be obtained by incubating a commercial Ivlg preparation in a bacterial growth medium. The next step was to try to determine which ingredients in the bacterial culture growth medium play a role in producing detectable autoantibodies.

First, Ivlg in 2% tryptic soy broth (TSB), (which contains peptones in a 17 to 3 ratio of pancreatic digest of casein to papaya digest of soy, respectively) (the remainder being water) was incubated at 37° C. for 20 hours with shaking. The incubated mixture was tested for the presence of aPL, and the result was negative.

Next, lvIg was incubated in a test tube in soy broth, sodium nitroprusside (SNP) and hemin (an iron (ferric) containing protoporphyrin) at 37° C. for 20 hours with shaking. The amounts used were 60 microliters of lvIg, 5 microliters of SNP and 5 microliters of hemin in a total of 1 ml of soy broth. The incubated mixture tested positive for the presence of aPL, particularly aPS (15 MoM) and aPE (41 MoM). (data not shown)

Example 21

A series of experiments was conducted to determine if incubation with hemin alone would be sufficient to cause the appearance of autoantibodies in lvIg or in plasma or serum.

Reconstituted lyophilized lvIg (at a concentration of 100 mg/ml) was added to and incubated in a phosphate buffered saline (PBS) solution with hemin for 20 hours at 37° C. The amounts used were 300 µl of lvIg solution and 5 µl of a hemin solution (75 µg) in a total volume 1 ml.

As shown in FIG. 21, the incubated mixture showed significant amounts of aPS and aPE IgG, and, to a lesser extent, aCL IgG.

When serum or plasma were incubated with hemin under similar conditions, no autoantibodies were detected.

Example 22

The fact that positive results for the presence of autoantibodies could be obtained when lvIg was incubated with hemin, whereas negative results were obtained when serum or plasma were incubated with hemin suggested that serum or plasma could contain substances that inhibit or interfere with the process of obtaining autoantibodies.

Figure 22:
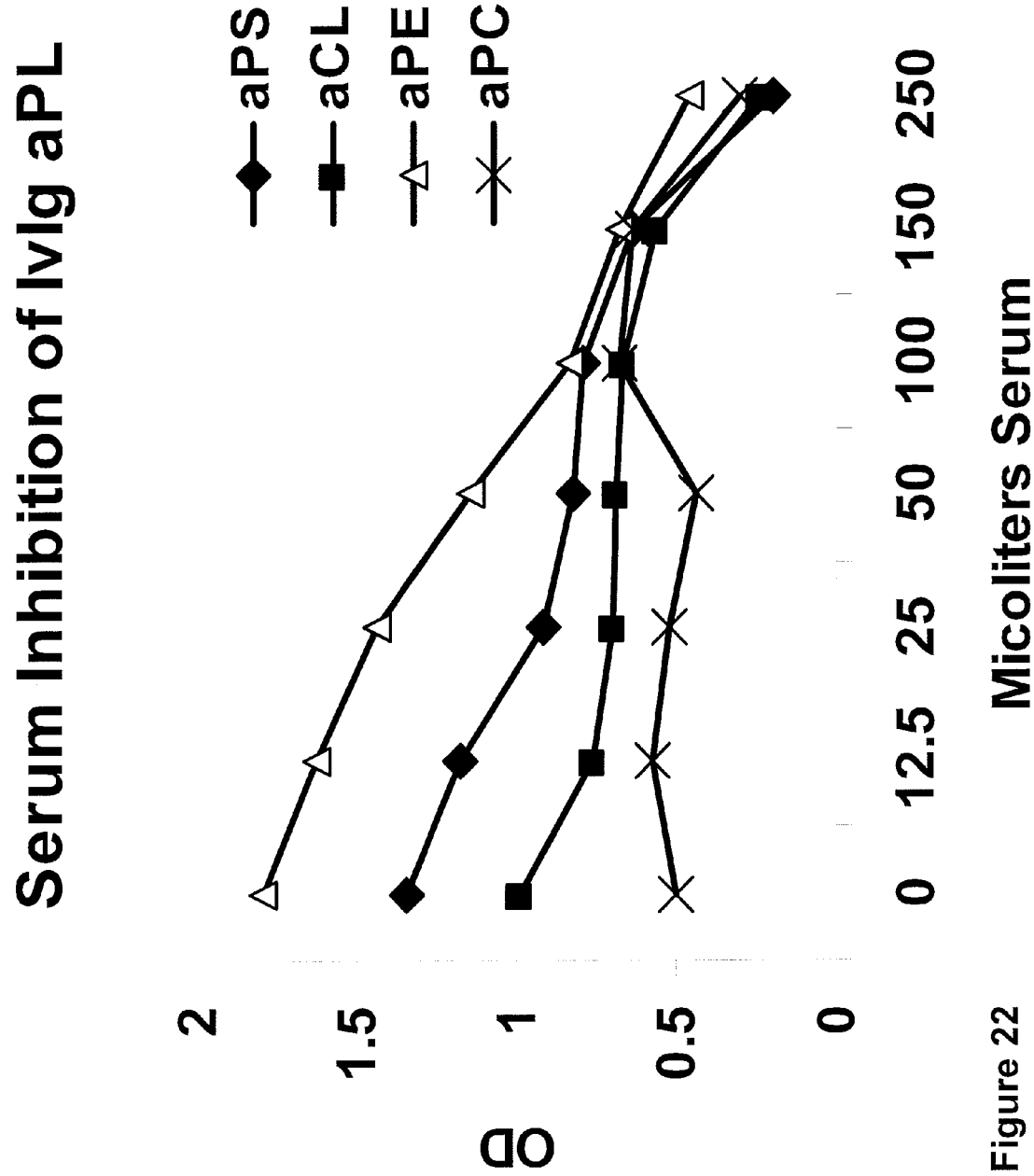
FIG. 22 is a graph showing the amount of aPS, aCL, aPE, and aPC (as measured by optical density, OD) detected in a series of lvlg preparations that were incubated with hemin, as a function of the amount of human serum (in µl) added to the preparations.

In a series of experiments, lvIg was incubated in a Tris buffer with hemin, for 20 hours at 37° C., similar to the process of Example 21, with the added feature that an increasing amount of human serum (the inventor's) was added to the batches before incubation. Each separate batch was tested for the presence of aPS, aCL, aPE and aPC autoantibodies, and the results are shown in FIG. 22. The results shown in FIG. 22 demonstrate that increasing amounts of serum did have an inhibitory effect on the release of antiphospholipid antibodies. Similar results were shown with substituting plasma for serum (data not shown). A possible explanation for these results is that hemin, which contains an iron molecule in its ferric state and which is known as an active oxidizing agent, may act to oxidize a binding site of certain immunoglobulin molecules so that the altered binding site is able to bind self antigens. This process may be inhibited by substances, perhaps antioxidants, in the blood.

Example 23

Figure 23:
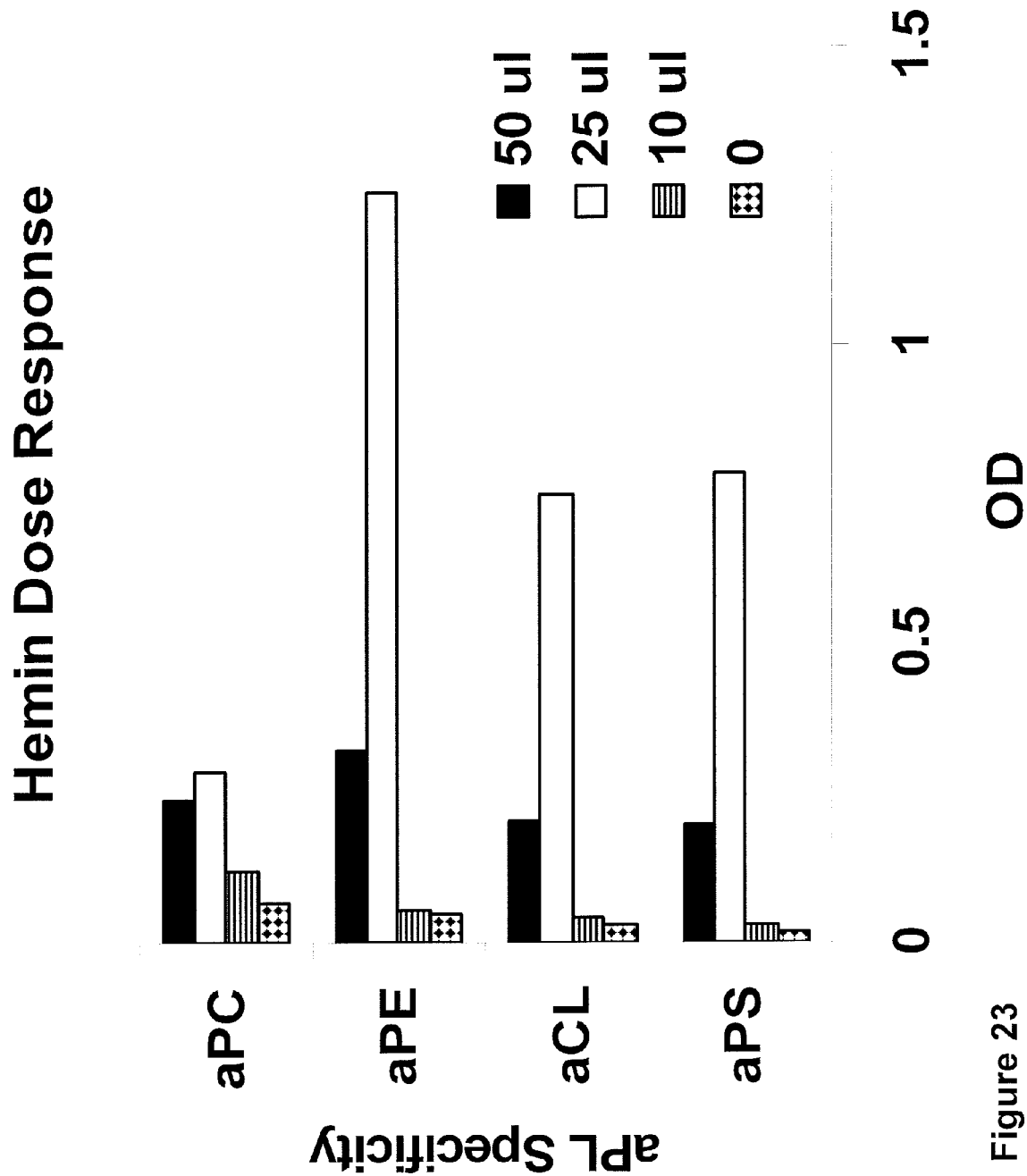
FIG. 23 is a graph showing the amount of aPS, aCL, aPE, and aPC (as measured by optical density, OD) detected in a series of diluted human serum preparations that were incubated with hemin, as a function of the amount of hemin (in µg) added to the preparations.

Human serum (the inventor's) was diluted 1/10 in Tris buffer. In a series of experiments, this diluted serum, in 1 ml batches, was incubated with an increasing amounts of hemin, specifically, 0 µl, 10 µl, 25 µl and 50 µl. (Previously, it had been found that hemin by itself was not sufficient to cause the release of autoantibodies from blood or serum, although it was sufficient to cause such release from lyIg. Therefore, the purpose of diluting the serum was to dilute the effect of any interfering substances found in the blood, such as antioxidants.) The batches were tested for the presence of aPS, aCL, aPE and aPC autoantibodies, and the results are shown in FIG. 23. The results shown in FIG. 23 show that while no significant amounts of autoantibodies were detected in diluted serum when 0 or 10 µl of hemin is added, significant amounts are detected with 25 µl of hemin. For an unknown reason, the amounts of detected autoantibodies were less with 50 µl of hemin.

Example 24

Figure 24:
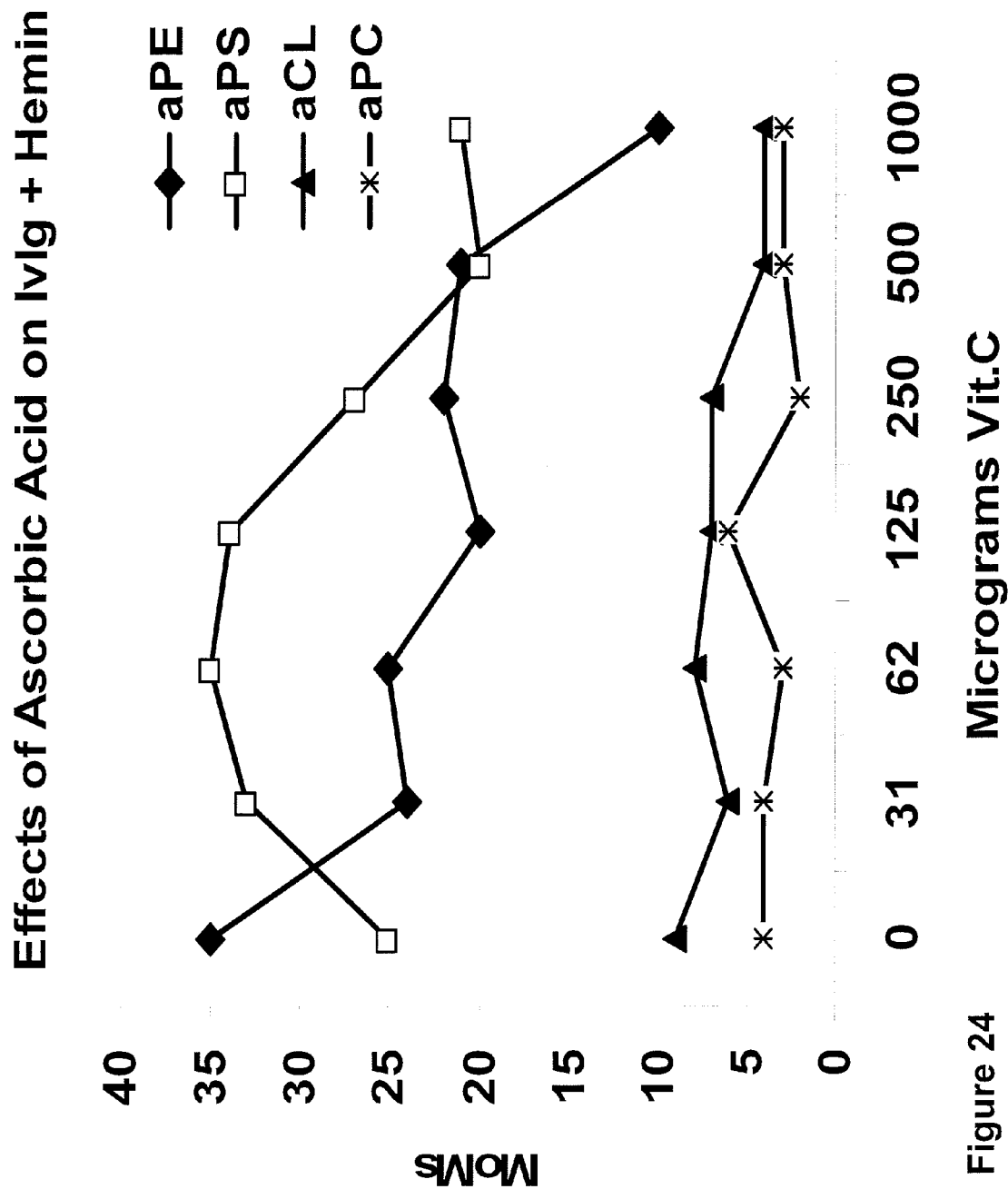
FIG. 24 is a graph showing the amount of aPS, aCL, aPE, and aPC (as measured by multiples of the mean, MoMs) detected in a series of lvlg preparations that were incubated with hemin and Vitamin C, as a function of the amount of Vitamin C (in µg) added to the preparations.

The next series of experiments was designed to determine if an antioxidant such as vitamin C, which is present in blood, would inhibit the release of autoantibodies. In a series of experiments, lvIg was incubated in a Tris buffer with hemin, with the added feature that an increasing amount of ascorbic acid (Vitamin C) was added to the hemin-containing buffer and allowed to mix for 30 minutes before adding the lvIg and before incubation. As shown in FIG. 24, there was about 78% inhibition of hemin-induced aPE release with 1 mg of Vitamin C, an amount that represents a physiological concentration of Vitamin C. There is a biphasic curve with aPS release, which raises the possibility that Vitamin C at low concentrations can act as an oxidizing agent, but becomes an antioxidant (reducing) agent at higher concentrations.

Example 25

Figure 25:
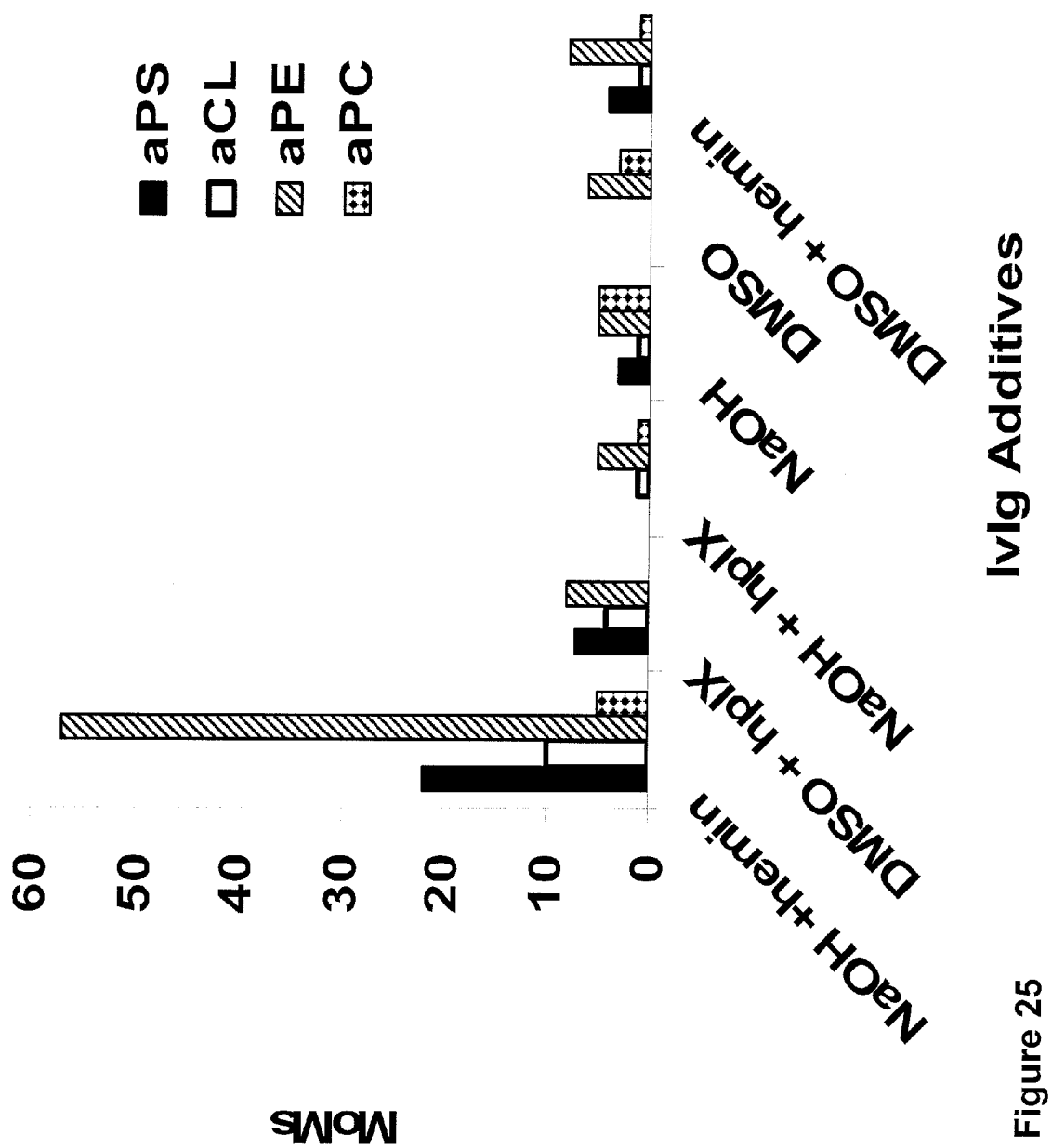
FIG. 25 is a graph showing the amount of aPS, aCL, aPE, and aPC (as measured by multiples of the mean, MoMs) detected in a series of lvlg preparations that were incubated with NaOH solubilized hemin, DMSO-solubilized hematoporphyrin IX (hpIX), NaOH-solubilized hpIX, NaOH alone, DMSO alone, and DMSO-solubilized hemin.

The next series of experiments was designed to determine whether the vehicle that hemin is dissolved in has an impact on the results obtained and whether the iron atom in hemin is necessary. In a series of experiments, lvIg was incubated in a Tris buffer with hemin, or with other additives. In particular, in one instance, hemin was solubilized with NaOH. In another instance, it was solubilized with DMSO. In other instances, hematoporphyrin IX (hpIX), which is the same molecule as hemin, but without the iron (Fe+++), was used in place of hemin and was solubilized with NaOH or DMSO. In other instances, NaOH and DMSO were tested as controls (without hemin or hpIX). As shown in FIG. 25, the use of NaOH solubilized hemin produced positive results for the presence of autoantibodies, whereas hemin+DMSO, hpIX+NaOH, hpIX+DMSO, NaOH alone, and DMSO alone did not produce positive results.

Example 26

Figure 26:
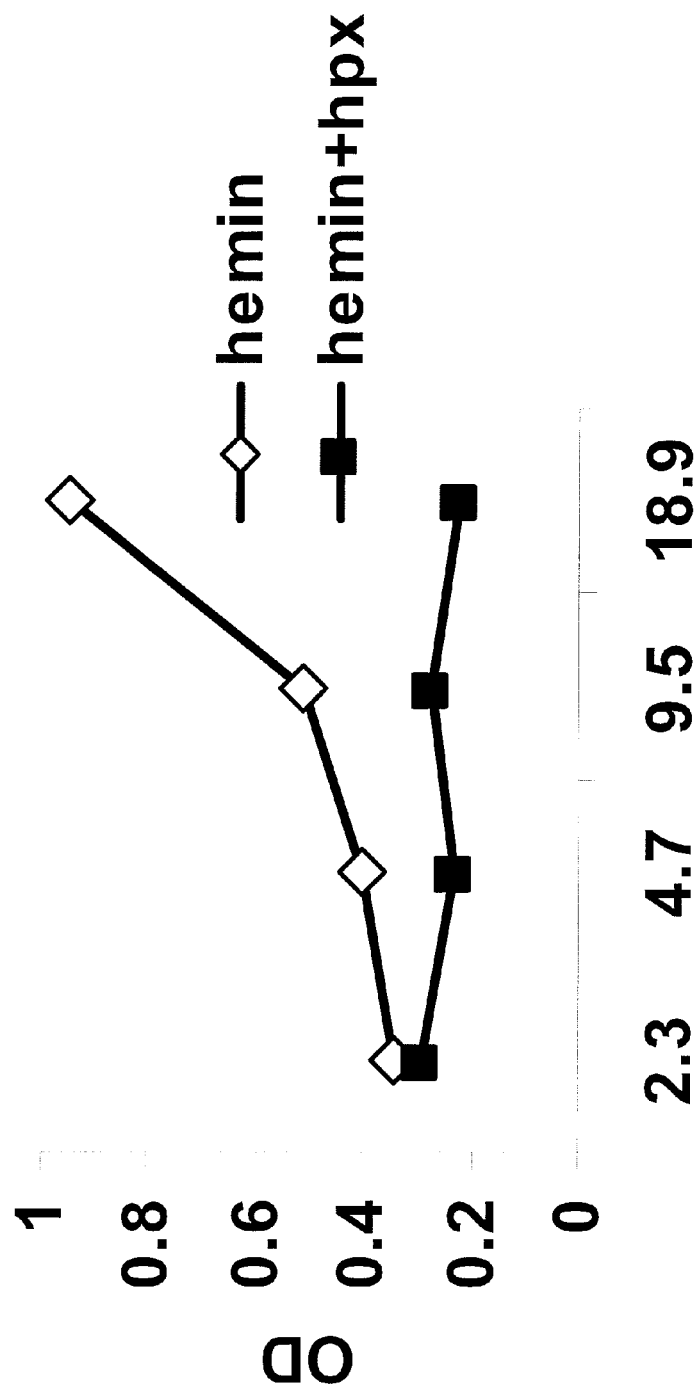
FIG. 26 is a graph showing the amount of aPS (as measured by optical density, OD) detected in a series of lvlg preparations that were incubated with increasing amounts of hemin and increasing amounts of hemin and hemopexin (hpx).

To further establish that hemin was causing oxidation of antibodies, equimolar amounts of hemopexin (Hpx) were added to the lvIg PBS hemin mixture. Hpx is an antioxidant molecule with an extraordinarily high binding affinity for heme iron. Lyophilized Hpx purchased from SciPac (Kent, England) was reconstituted in PBS at 10 mg/ml. Shown in FIG. 26 are the aPS redox data resulting from adding increasing concentrations of hemin to the lvIgG countered with adding equamolar concentrations of Hpx. Because there is an 1:1 binding interaction between hemin and Hpx, the Hpx was able to negate the redox capability of the ferric iron present in hemin.

Example 27

Figure 27:
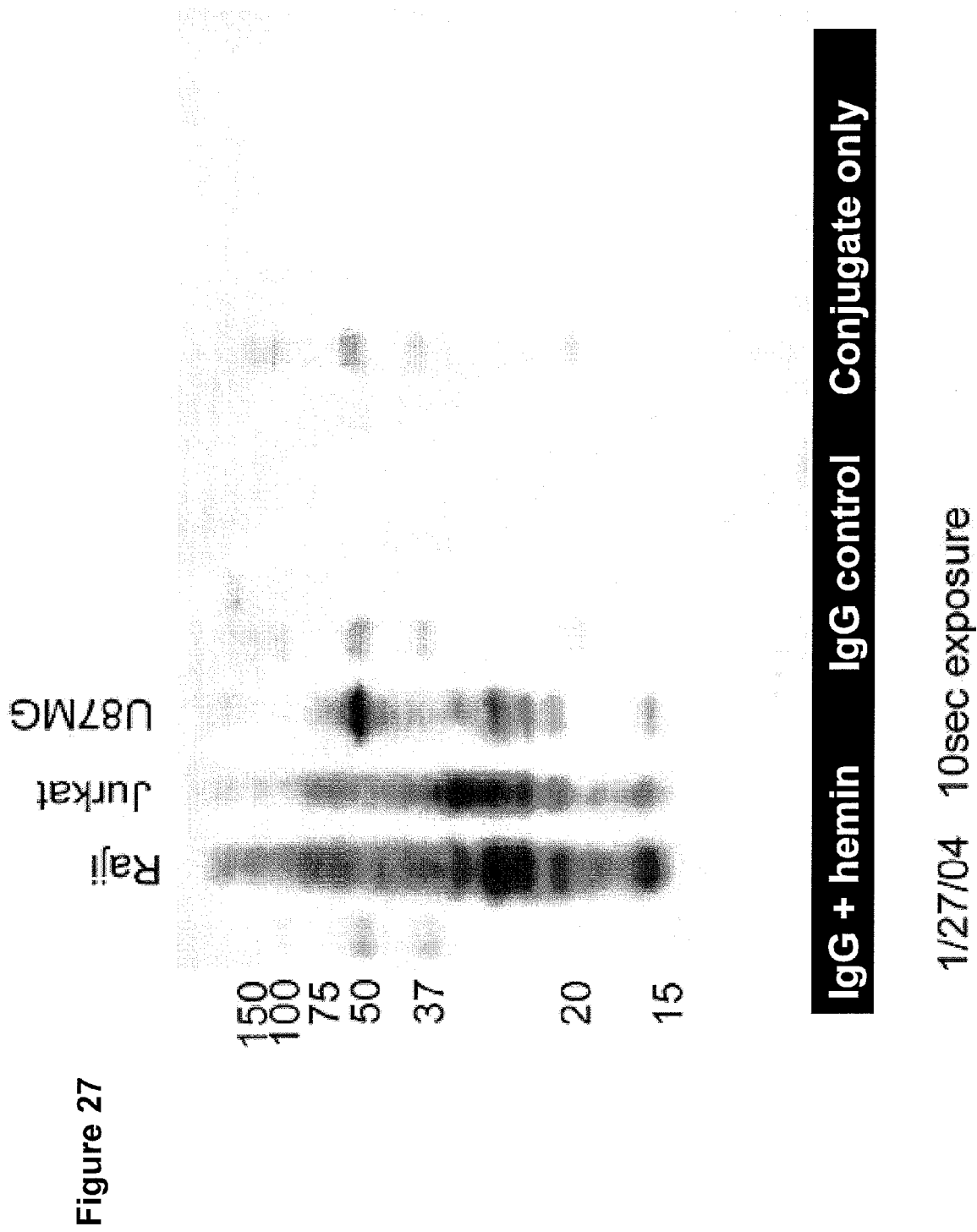
FIG. 27 shows the Western blots obtained for three cell lysates with hemin-treated lvlg and untreated lvlg used as primary antibodies, along with a blot wherein anti-human HRP-tagged conjugate was used as a control.

To illustrate the broad range and activity of autoantibodies that can be obtained by an oxidation treatment of lvIg, a series of Western blots were set up using cell lysates from 3 different cell lines using hemin-treated lvIg or untreated lvIg as primary antibodies and using anti-human HRP-tagged conjugate as a control (HRP=horseradish peroxidase). The blots are shown in FIG. 27. The "B" lysate is a B lymphocyte cell line called Raja from a patient with a lymphoma. The "T" lysate is a T-lymphocyte-derived cell line called Jurkat again from a leukemic patient. The U87MG lysate is a glioblastoma blast cell line (brain cancer). The reduced lysates were run into the gel at 50 mg/ml concentration. To obtain the hemin-treated lvIg preparation, 75 μg of hemin was combined with 1 ml of PBS containing 6 mg of lvIgG. Incubation was for 20 hours at 37 degrees. In FIG. 27, the blot wherein hemin-treated lvIg was used as the primary antibodies is labeled "Test IgG; the blot wherein untreated lvIg was used as the primary antibodies is labeled "Control", and the blot to which anti-human HRP-tagged conjugate was applied without primary antibodies is labeled "Secondary". The hemin-treated and untreated IgG preparations were diluted 1/1000 respectively. The anti-human HRP-tagged conjugate was used at a dilution of 1/5000.

These data clearly show that the hemin-treated lvIg has abundant activity towards human cellular components in comparison to untreated lvIgG and the conjugate control, which do not.

Example 28

The next experiment was carried out to determine whether oxidizing agents other than hemin, and in particular, oxidizing agents that do not contain iron, would be effective to unmask autoantibodies. A mixture of 25 μg of potassium permanganate ($KMnO_4$) at a concentration of 100 μM, and 2 mg of lvIg in a total volume of 1 ml of phosphate buffered saline was incubated overnight at 37° C. In the incubated mixture, aPC and aPS could be detected. aCL was usually detected, but not aPE (data not shown). It was later determined that a reason why aPE is not detected is because $KMnO_4$ alters the PE phospholipid antigen used in the ELISA testing.

Example 29

Figure 28A:
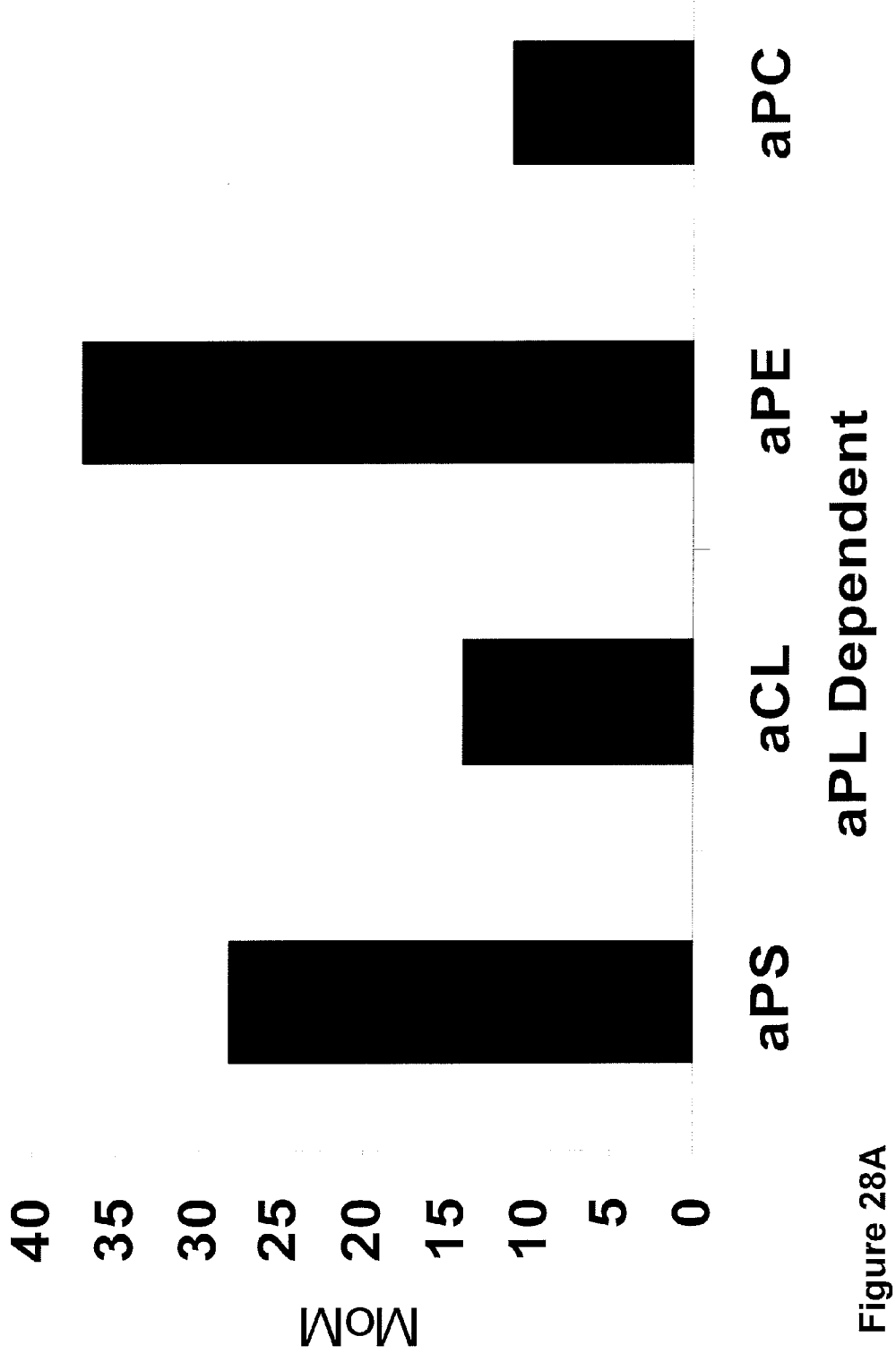
FIGS. 28A and 28B are graphs showing the amount of aPL dependent and aPL independent aPS, aCL, aPE, and aPC (as measured by multiples of the mean, MoMs) detected in a series of lvlg preparations in which electrodes connected to a 9 volt battery were immersed in a phosphate buffered saline solution containing the lvlg for 2 minutes.
Figure 28B:
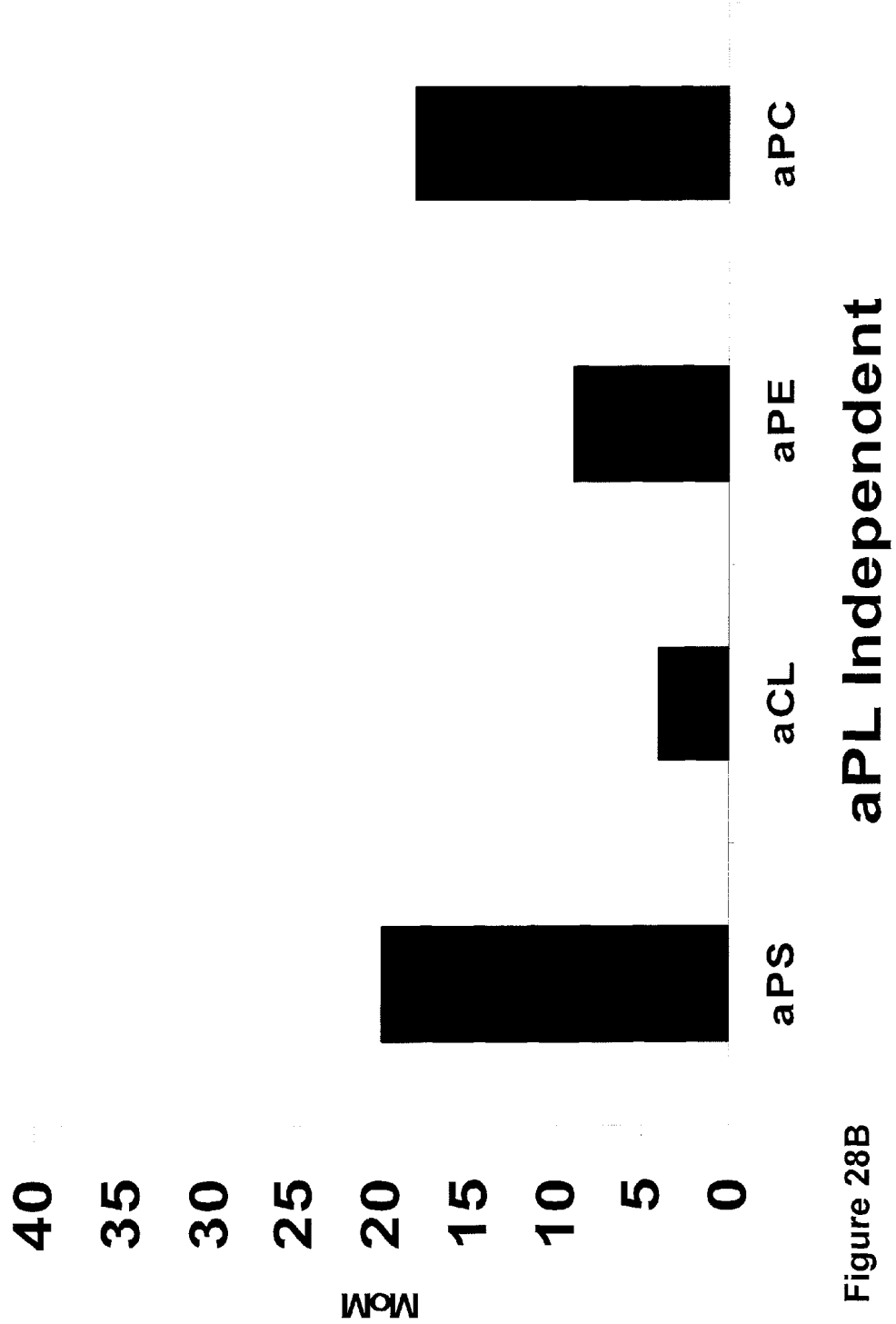

After it was shown that autoantibodies could be unmasked by oxidation reactions, the next question was whether electrochemical methods, such as an electromotive force from a battery, could achieve the same effect.

lvIg was dissolved in a phosphate buffered saline solution, and, in separate experiments, galvanized steel, copper, or stainless steel electrodes were connected to the positive and negative terminals of a 9-volt battery and were submersed into the solution for 1-2 minutes. During this period, bubbling was noticed in the solution and the PBS solution changed color (blue when copper wires were used, brown when stainless steel wires were used and green when galvanized steel wires were used). As shown in FIGS. 28A and 28B, the treated solution tested positive for the presence of aPS, aCL, aPE and aPC autoantibodies, in aPL dependent testing, and positive for the presence of aPS, aPE and aPC autoantibodies in aPL independent testing.

Example 30

Figure 29:
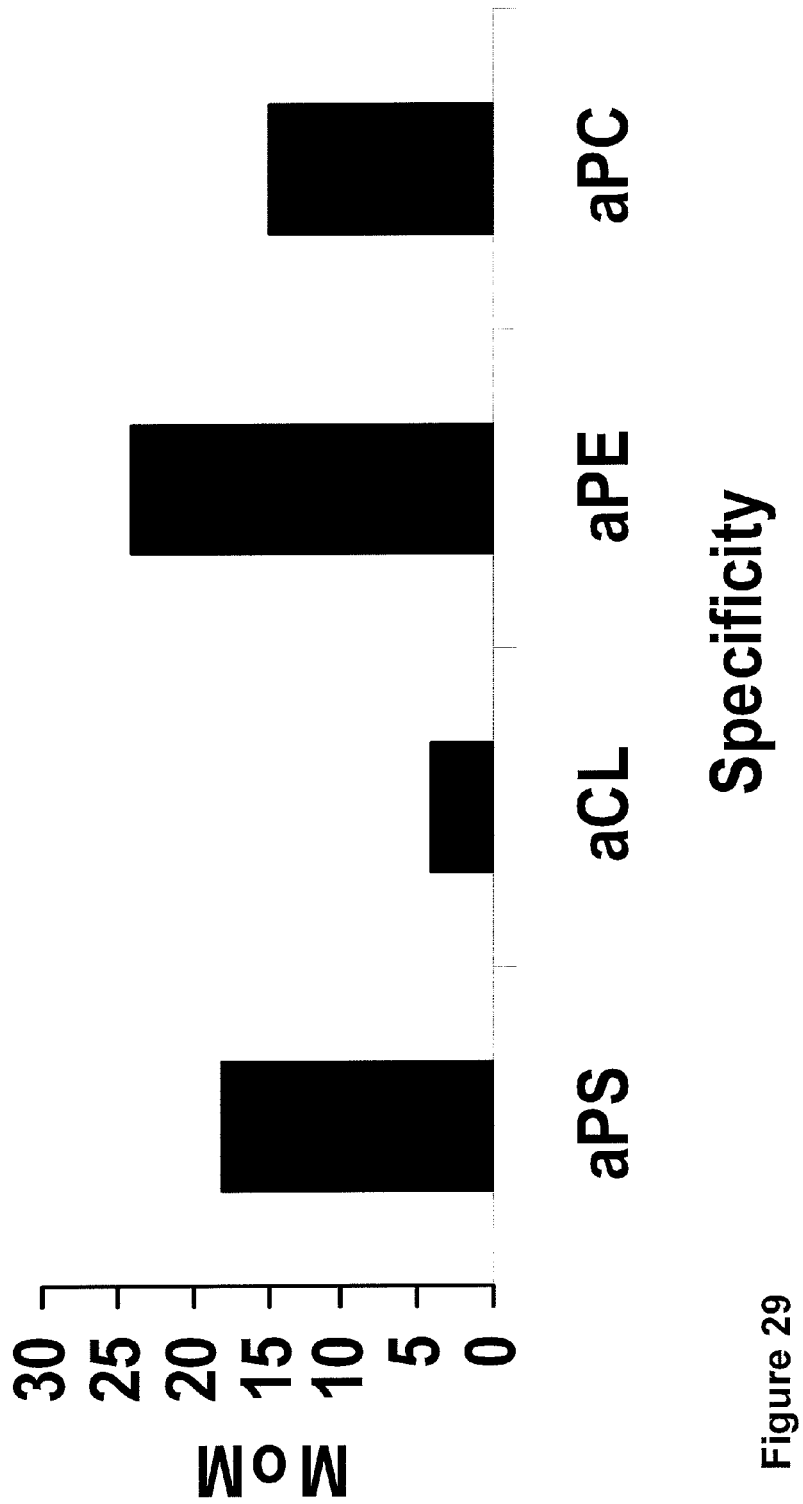
FIG. 29 is a graph showing the amount of aPS, aCL, aPE, and aPC (as measured by multiples of the mean, MoMs) detected in a series of lvlg preparations in which electrodes connected to a 6 volt battery were immersed in a phosphate buffered saline solution containing the lvlg for 60 seconds.

To avoid the interaction of metals with the solution and thereby determine the effect only of an electric current, graphite electrodes were used in place of the metal electrodes. Graphite is inert, but is able to pass electrons into conducting solutions without participating in reactions.

lvIg was dissolved in a phosphate buffered saline solution, and graphite electrodes connected to the positive and negative terminals of a 6-volt battery were submersed into the solution for 60 seconds. As shown in FIG. 29, the treated solution tested positive for the presence of aPS, aPE and aPC autoantibodies.

Example 31

In the experiments involving applying electric current to solutions of lvIg in phosphate buffered saline, a significant increase in pH was noticed, possibly due to the formation of NaOH. In order to keep the reactions at physiological pH levels, a cell culture medium, RMPI, was substituted for the phosphate buffered saline.

Figure 30:
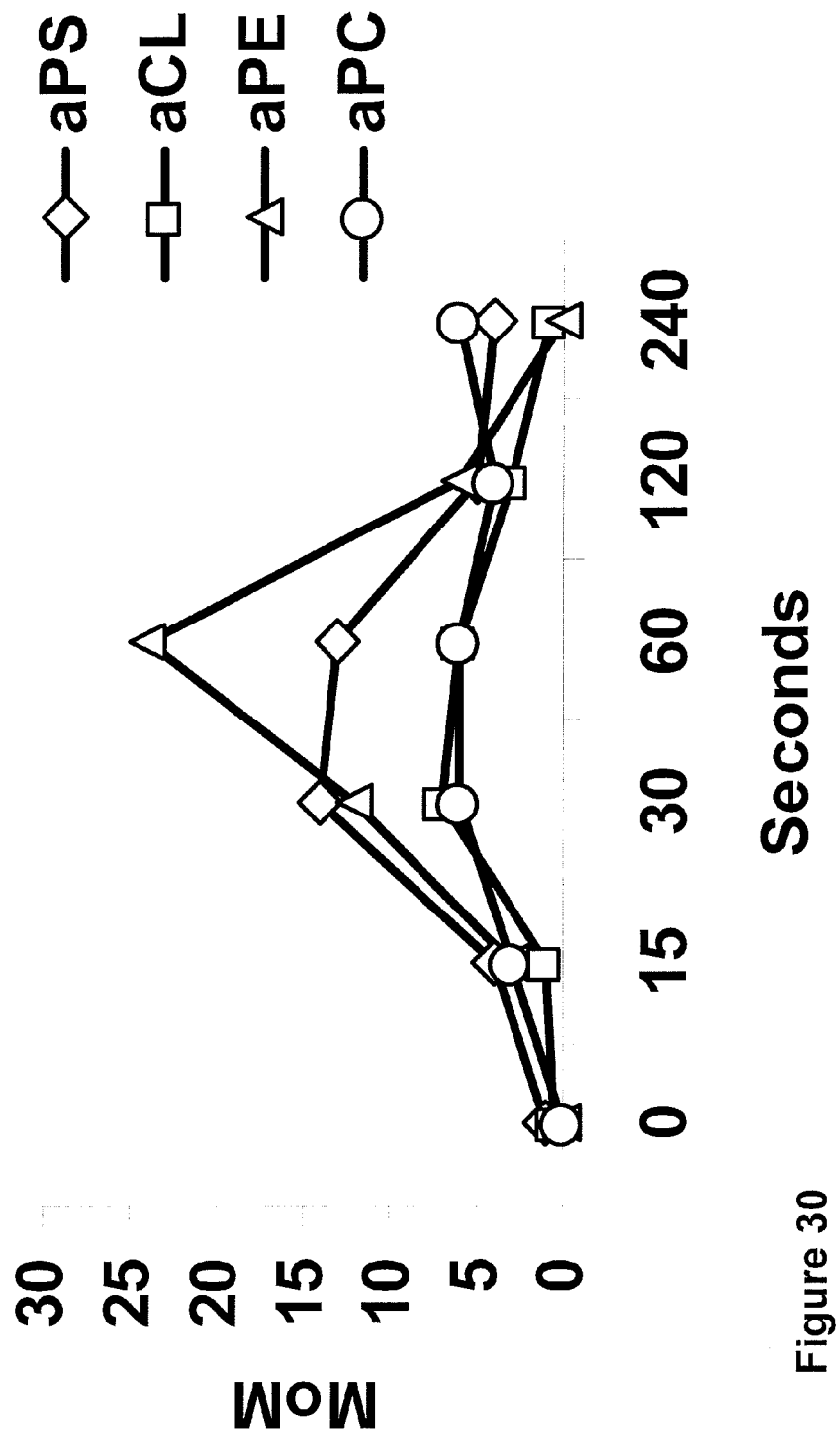
FIG. 30 is a graph showing the amount of aPS, aCL, aPE, and aPC (as measured by multiples of the mean, MoMs) detected in a series of lvlg preparations in which electrodes connected to a 6 volt battery were immersed in a phosphate buffered saline solution containing the lvlg, as a function of the time of immersion.

The next series of experiments was carried out to determine the effects of the time of exposure to the electric current on the unmasking of autoantibodies. lvIg was dissolved in RMPI, a cell culture medium and graphite electrodes connected to the positive and negative terminals of a 6-volt battery were submersed into the solution for a variable amount of time. As shown in FIG. 30, the maximum release of dependent aPL was obtained after 60 seconds of exposure to the current. Curiously, between 2 minutes and 4 minutes, the amount of aPL declined or disappeared.

Example 32

Since the previous experiment had shown that aPL antibodies could be obtained from lvIg after exposure to an electric current, but that the aPL antibodies disappeared after further exposure to the current, the next question was whether the unmasking of autoantibodies could be reversed by an electric current. That is, could a positive control serum be treated so that autoantibodies were no longer detectable?

Figure 31A:
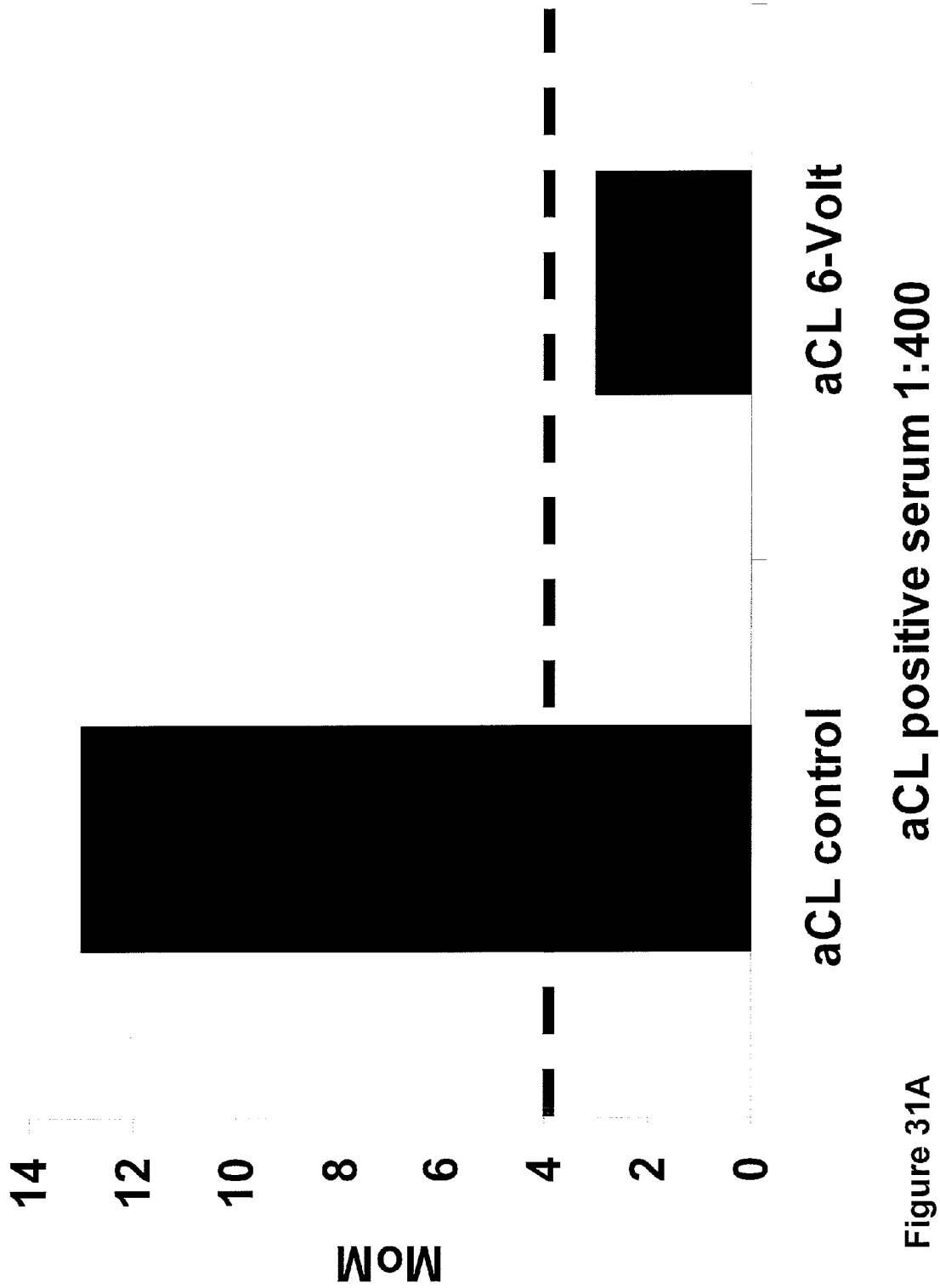
FIGS. 31A, 31B and 31C are graphs showing the amount of aCL, aPE, and aPS, respectively (as measured by multiples of the mean, MoMs), detected in control solutions before and after exposure for 240 seconds to electrodes connected to a 6 volt battery.
Figure 31B:
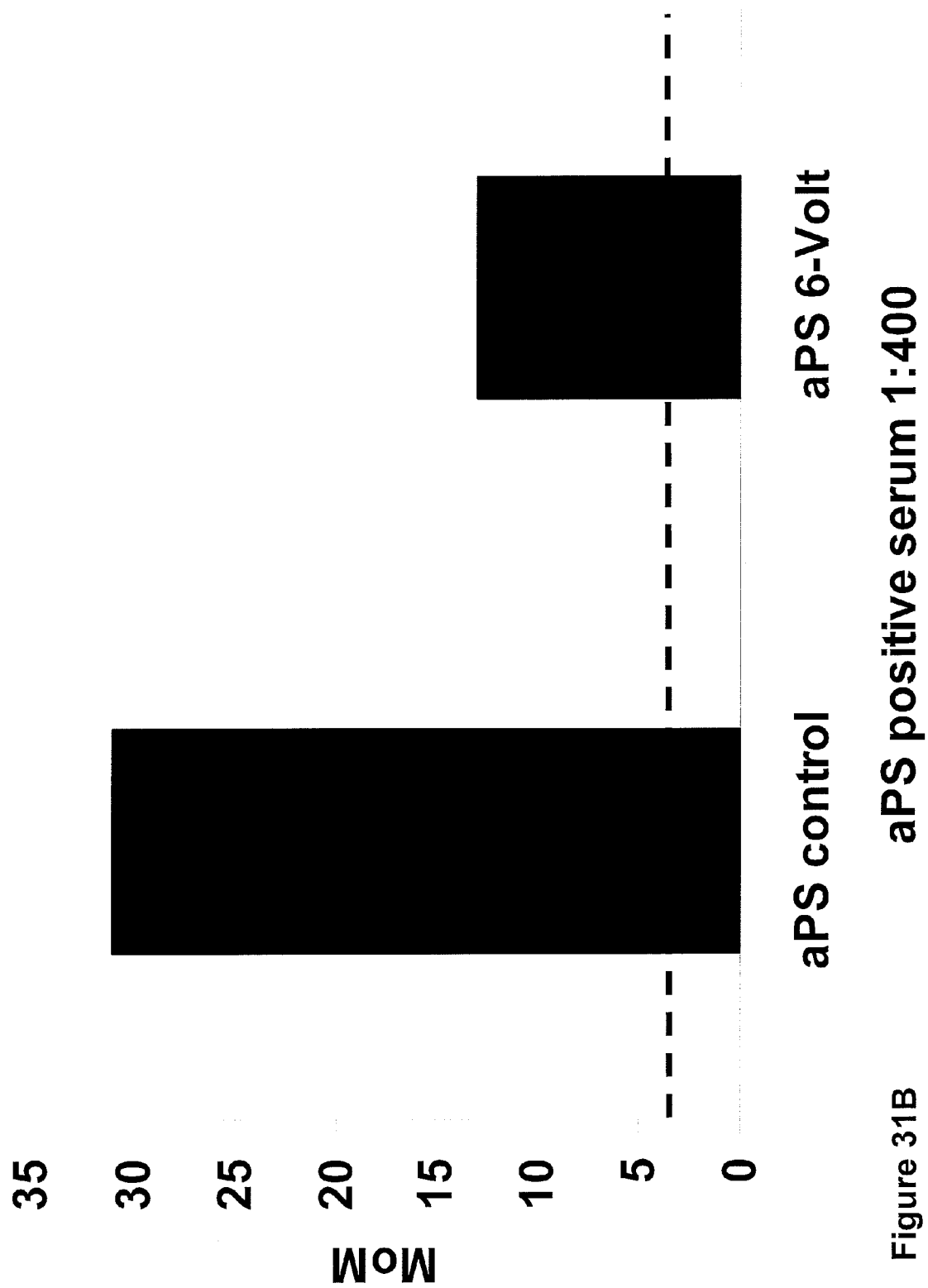
Figure 31C:
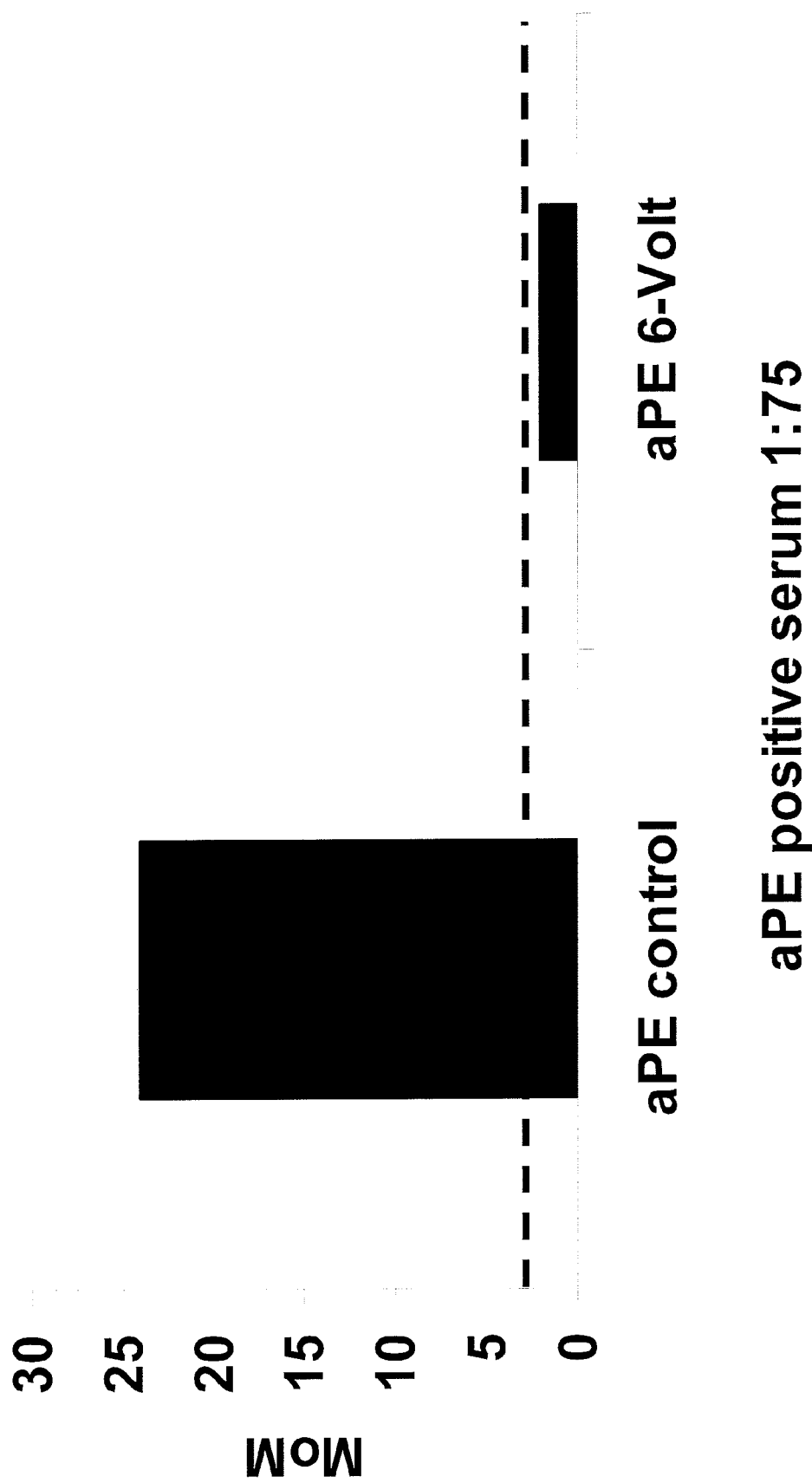

In separate experiments, aCL positive control serum, at a dilution of 1:400, aPE positive control serum at a dilution of 1:75, and aPS at a dilution of 1:400 were exposed to an electric current by immersing graphite electrodes connected to the positive and negative terminals of a 6-volt battery for up to 240 seconds. As shown in FIGS. 31A-31C, each control sera became negative for its respective specificity.

Example 33

Figure 32:
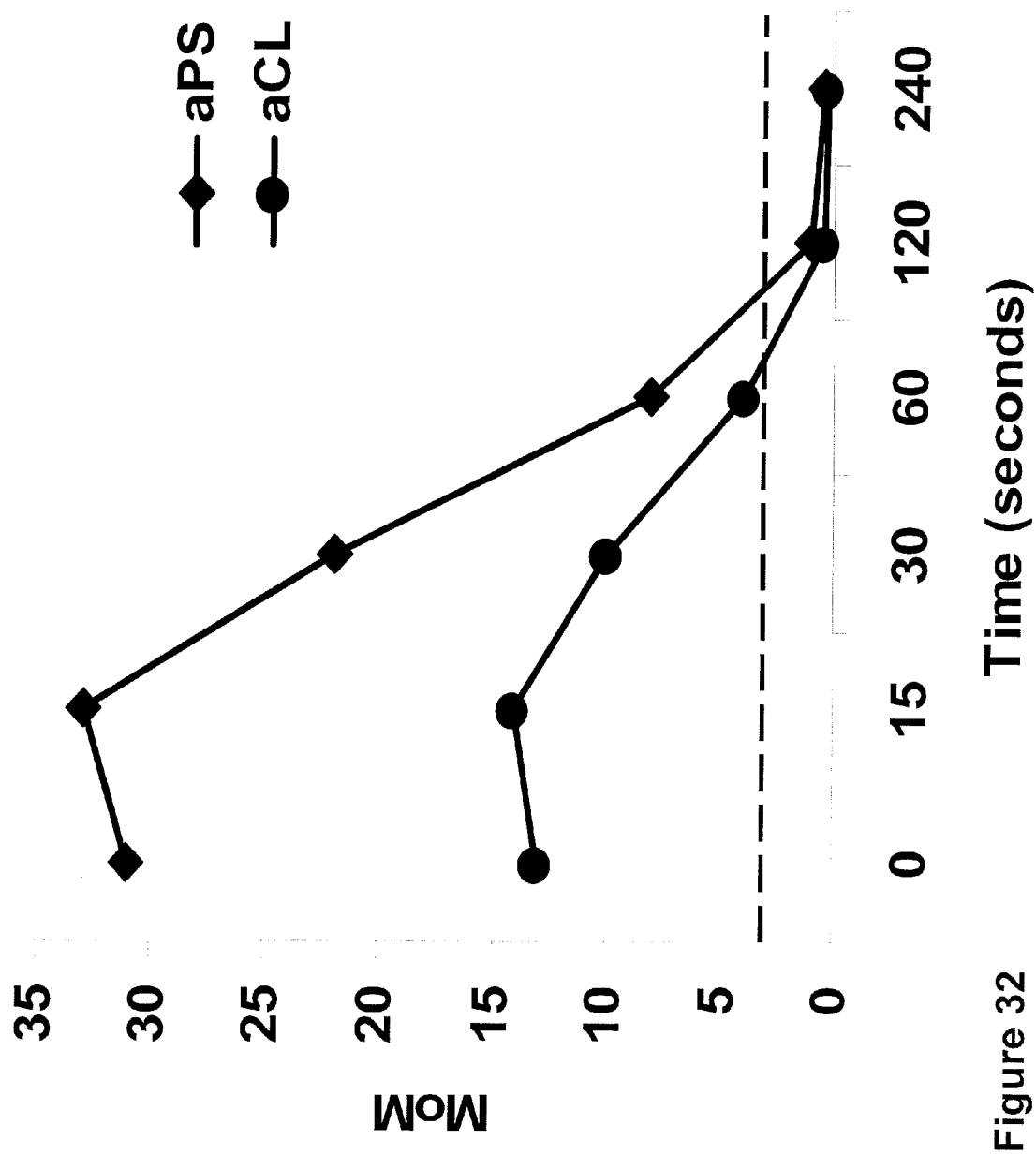
FIG. 32 is a graph showing the amount of aPS and aCL, respectively (as measured by multiples of the mean, MoMs), detected in the PBS-diluted serum of an aPS and aCL-positive patient. In the experiment, graphite electrodes connected to a 6 volt battery were immersed in the diluted serum for a variable amount of time.

Based on the results in Example 32, the next question that was asked was whether autoantibodies of a patent having an autoimmune disease could be remasked if the patient serum was exposed to an electric current. Serum from a patient having elevated levels of aPS and aCL was diluted 1/400 with phosphate-buffered saline (the dilution in PBS was in an amount that would achieve an OD value of 1.000 in 10-15 minutes) and graphite electrodes connected to the positive and negative terminals of a 6-volt battery were submersed into the solution for a variable amount of time. As shown in FIG. 32, the amount of aCL and aPS detectable in the samples of the autoimmune patient's serum declined significantly after 30 seconds and was no longer detectable after 2 minutes. These experiments were repeated for other patients' antibodies and the same result was obtained (data not shown).

Example 34

In an early experiment, a blood sample from a patient who had a very specific and high titer IgA aPE was exposed to hemin in a routine microbiology culture bottle. It was observed that after exposure to hemin her IgA aPE disappeared, and the emergence of IgG aPS, aCL and most spectacularly, IgG aPE was detected in the aPL ELISA. At the time, an explanation for this phenomenon was not readily apparent.

Figure 33:
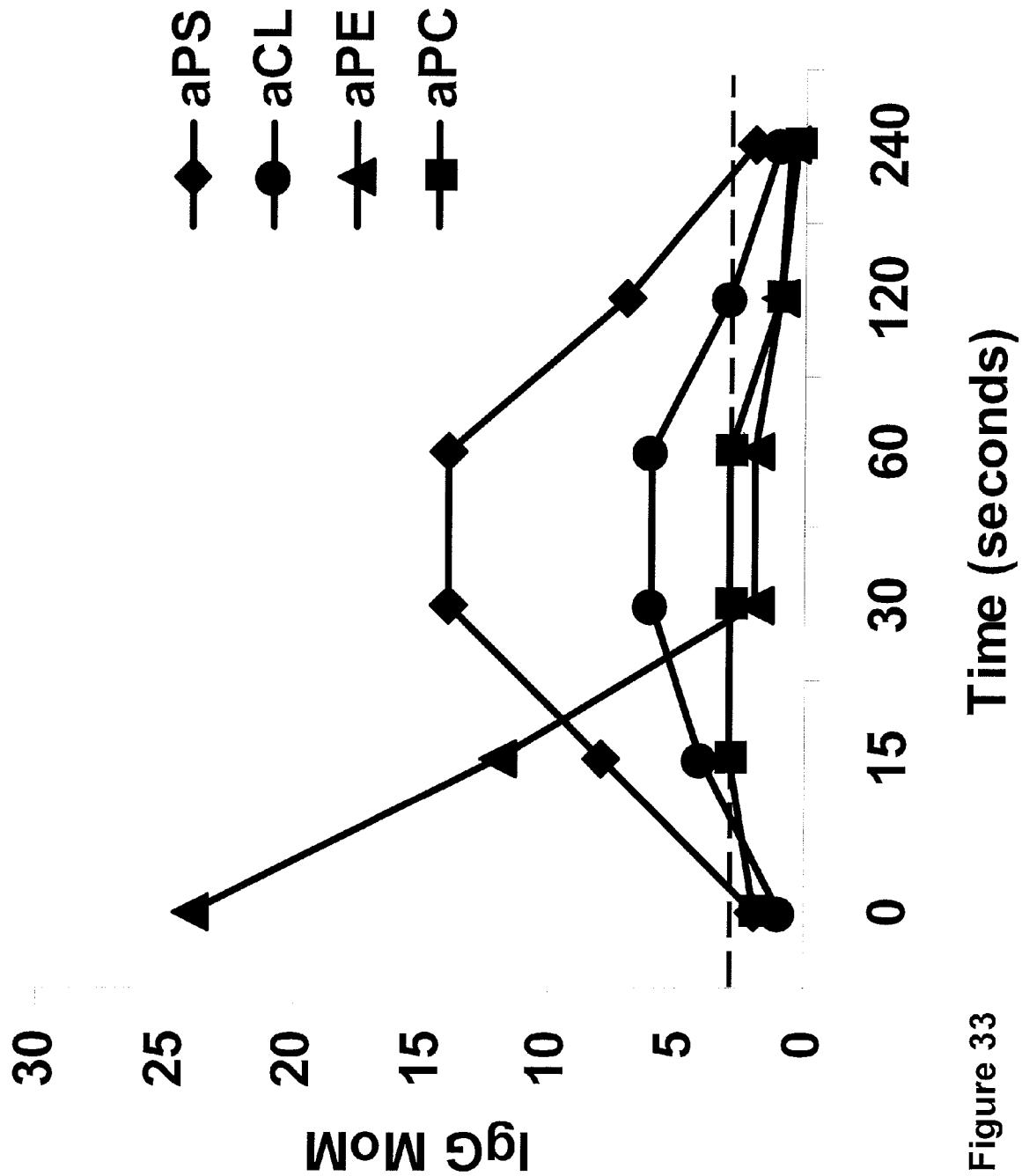
FIG. 33 is a graph showing the amount of aPS, aCL, aPE, and aPC (as measured by multiples of the mean, MoMs), respectively, detected in the PBS-diluted serum of an aPE-positive patient. In the experiment, graphite electrodes connected to a 6-volt battery were immersed in the diluted serum for a variable amount of time.

With the discovery of a faster unmasking process using electric current, it became possible to confirm the earlier results with another patient having a high aPE. In this experiment, serum from a patient having a high aPE was diluted in PBS by 1/5 and graphite electrodes connected to the positive and negative terminals of a 6-volt battery were submersed into the solution for a variable amount of time. As shown in FIG. 33, the aPE became undetectable (masked) within 30 seconds of a 6-volt DC current application, with a concomitant unmasking and detection of aPS and aCL IgG. The newly unmasked aPL peaked around 30 seconds only to become masked again after 2-4 minutes of exposure.

An important technical aspect addressed by the above experiment was that the patient aPE was treated apart from the plasma protein diluent used in the assay, in the present case, 10% adult bovine plasma (ABP). In other experiments not shown, the diluted patient sera were exposed to 6-volt EMF conditions before adding the plasma proteins used in the ELISA diluent. The important aspect of these experiments was to show that the EMF effects were being applied to the patients' antibodies and not to EMF changes in the plasma proteins used in the diluent.

These experimental data support the observations that redox reactions are determining the appearance and disappearance of different antibody specificities. What is also learned from these experiments is that the redox effects appear to be limited to the antibody binding site(s), the Fab portion of the antibody molecule. This is because the heterologous antihuman antibody-labeled conjugates used in the ELISA are not affected as the conjugates continue to recognize the different antibody heavy chain targets (Fc portions) of the antibody molecules. Thus, as the human antibody is not consumed or destroyed by redox, the most plausible explanation is that the antibody-binding site in the Fab portion of the antibody molecule contains accessible electrons that can participate in the oxidation/reduction process.

Example 35

Figure 34:
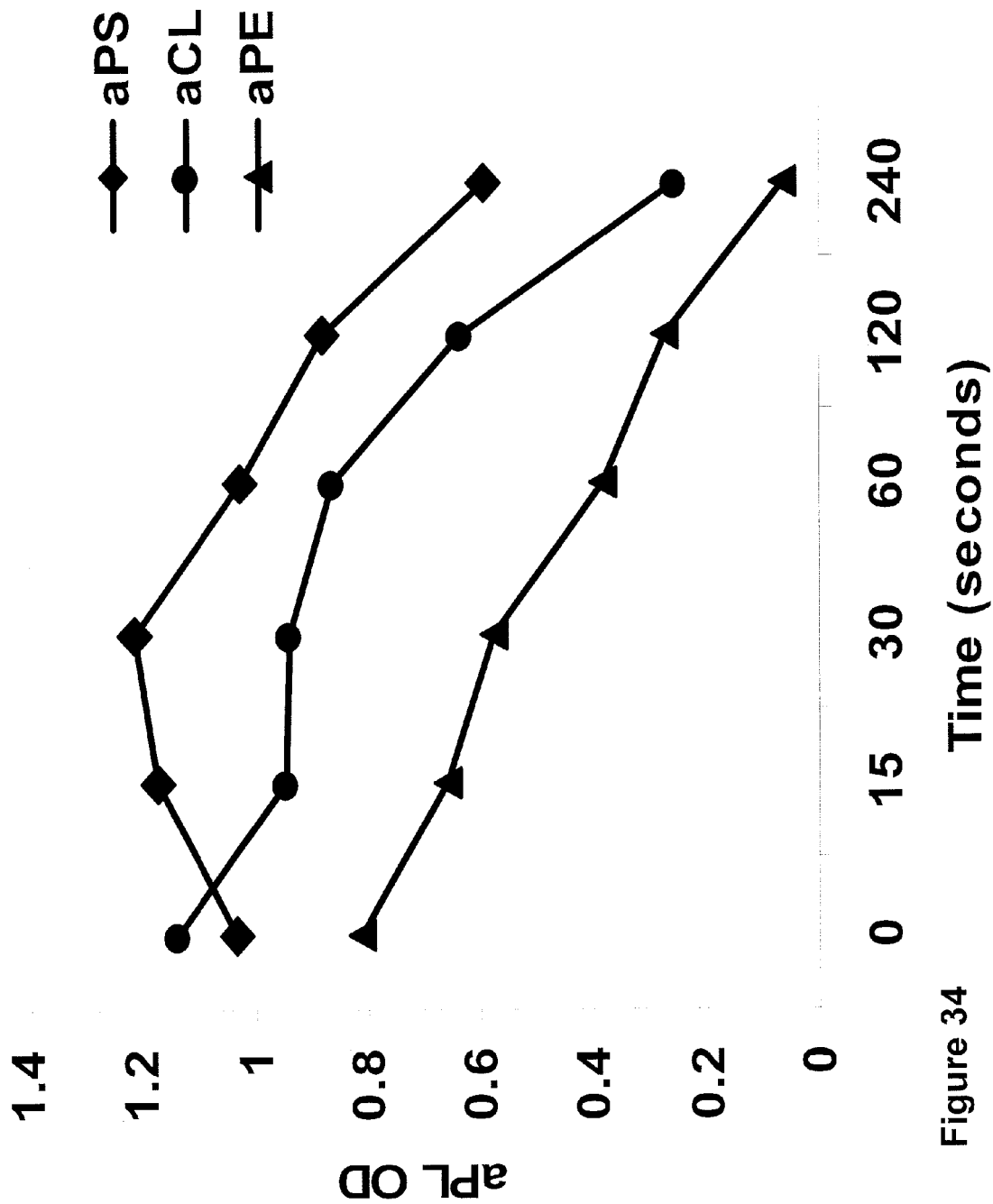
FIG. 34 is a graph showing the amount of aPS, aCL and aPE, (as measured by optical density, OD), respectively, detected in the PBS-diluted serum of an aPE-positive patient. In the experiment, the 10% adult bovine plasma (ABP) used in the determination of protein-dependent aPL binding was treated by immersing graphite electrodes connected to a 6-volt battery in the ABP for a variable amount of time.

The next experiments were carried out to see whether plasma proteins other than autoantibodies can have their binding specificity altered by oxidation-reduction. In these experiments, a 10% adult bovine plasma (ABP) solution, the same solution containing phospholipid-binding proteins that had been used to determine protein-dependent aPL binding, was exposed to an electric current from a 6-volt battery for a variable period of time. The treated ABP samples were then used in ELISA assays with aPS—, aCL—and aPE—positive patient sera to see if the treatment of the ABP would affect the outcome of the ELISA. As shown in FIG. 34, at time zero (untreated ABP), the positive patient sera give the aPL response in ABP that is routinely seen. As the 10% ABP is exposed to oxidation-reduction (EMF) over time, amount of aPL detected diminishes and after 2 minutes, the aPE positive serum is no longer positive. These results indicate that the plasma proteins that are responsible for the patients' aPL reactivity are altered by the exposure to the electric current. For example, as kininogen is the plasma protein responsible for providing a positive ELISA signal for aPE dependent reactions (the kininogen binds to PE, then the antibody binds to the kininogen, the aPE however will not bind to either PE or kininogen independently), this shows that the kininogen in the ABP sample is being altered by the redox exposure. aCL is also negative at 240 seconds exposure and since this patient serum requires either prothrombin and/or beta2 glycoprotein (or both could be involved) for producing a positive signal in the aPL ELISA, these two proteins must also be altered by the redox reactions. The same two plasma proteins are involved in the aPS example.

Obviously, many modifications and variations of the present invention are possible in light of the above teachings. It is therefore to be understood that, within the scope of the appended claims, the invention may be practiced otherwise than as specifically described.

I claim:

1. A method comprising the steps of
providing a composition comprising at least antibody suspended or dissolved in a liquid medium, the at least one antibody having a binding specificity that can be altered by a change in its redox state, and then
exposing the composition to an oxidizing agent or DC current sufficient to reversibly alter the binding specificity of the at least one antibody.

2. The method of claim 1 wherein said liquid medium is diluted whole blood, serum, or plasma.

3. The method of claim 1 wherein the composition comprises intravenous immunoglobulin (IvIg) suspended or dissolved in a liquid medium.

4. The method of claim 1 wherein the at least one antibody is an antibody of IgG, IgA, or IgM isotype.

5. The method of claim 1 wherein the at least one antibody is an autoantibody of IgG, IgA, or IgM isotype.

* * * * *